United States Patent
Sauer et al.

(10) Patent No.: US 10,806,511 B1
(45) Date of Patent: Oct. 20, 2020

(54) PARTIALLY INSULATED FOCUSED RADIOFREQUENCY ABLATION CATHETER

(71) Applicants: William Sauer, Newton, MA (US); Duy Nguyen, Palo Alto, CA (US)

(72) Inventors: William Sauer, Newton, MA (US); Duy Nguyen, Palo Alto, CA (US)

(73) Assignees: William Sauer, Newton, MA (US); Duy Nguyen, Palo Alto, CA (US)

( * ) Notice: Subject to any disclaimer, the term of this patent is extended or adjusted under 35 U.S.C. 154(b) by 975 days.

(21) Appl. No.: 14/942,442

(22) Filed: Nov. 16, 2015

Related U.S. Application Data

(60) Provisional application No. 62/079,992, filed on Nov. 14, 2014, provisional application No. 62/114,371, filed on Feb. 10, 2015.

(51) Int. Cl.
*A61B 18/14* (2006.01)
*A61B 18/00* (2006.01)

(52) U.S. Cl.
CPC ............ *A61B 18/1492* (2013.01); *A61B 2018/00083* (2013.01); *A61B 2018/00095* (2013.01); *A61B 2018/00119* (2013.01); *A61B 2018/00351* (2013.01); *A61B 2018/00577* (2013.01); *A61B 2217/007* (2013.01)

(58) Field of Classification Search
CPC .......... A61B 2018/00119; A61B 2018/00095; A61B 2018/00351
See application file for complete search history.

(56) References Cited

U.S. PATENT DOCUMENTS

| | | | | |
|---|---|---|---|---|
| 2002/0049438 | A1* | 4/2002 | Sharkey ............. | A61B 18/1402 606/41 |
| 2002/0120265 | A1* | 8/2002 | Fowler ............... | A61B 18/1485 606/45 |
| 2008/0091193 | A1* | 4/2008 | Kauphusman ..... | A61B 18/1492 606/41 |
| 2010/0174283 | A1* | 7/2010 | McNall, III ....... | A61B 18/1485 606/45 |
| 2012/0303002 | A1* | 11/2012 | Chowaniec ...... | A61B 17/07207 606/1 |

(Continued)

OTHER PUBLICATIONS

Nath S, et al., Basic Aspects of Radiofrequency Catheter Ablation. J Cardiovasc Electrophysiol. 1994;5:863-876.

(Continued)

*Primary Examiner* — Michael F Peffley
*Assistant Examiner* — Bo Ouyang
(74) *Attorney, Agent, or Firm* — David G. Rosenbaum; Rosenbaum IP, P.C.

(57) ABSTRACT

Partially insulated focused ablation (PIFA) catheters using thermally conductive materials have differential radiofrequency (RF) heating and thereby allow for tailored RF application. Open-irrigated, 4 mm, and 8 mm RF ablation catheters were partially insulated by coating half their surfaces with a layer of vinyl, silicone, vinyl-silicone, polyurethane, or a composite of aluminum oxide/boron nitride (AOBN). RF ablation using catheter tips partially coated with a thermally conductive insulation material such as AOBN results in larger ablation lesion volumes without being limited by standard temperature controls. Partial insulation of the catheter tip is able to protect adjacent critical structures during in vivo ablation.

22 Claims, 33 Drawing Sheets

(56) References Cited

U.S. PATENT DOCUMENTS

2013/0090650 A1* 4/2013 Jenson .............. A61B 18/1492
606/41

OTHER PUBLICATIONS

Haines D., et al., Observations on Electrode-Tissue Interface Temperature and Effect on Electrical Impedance During Radiofrequency Ablation of Ventricular Myocardium. Biophysics of ablation: Application to technology. J Cardiovasc Electrophysiol 2004; 15:S2-S11.

Langberg JJ, et al., Radiofrequency Catheter Ablation; The Effect of Electrode Size on Lesion Volume In Vivo. Pacing Clin Electrophysiol. 1990;13:1242-1248.

Otomo K, et al., Why a large tip electrode makes a deeper radiofrequency lesion: effects of increase in electrode cooling and electrode-tissue interface area. J Cardiovasc Electrophysiol. 1998;9:47-54.

Haines DE, et al., Observations on electrode-tissue interface temperature and effect on electrical impedance during radiofrequency ablation of ventricular myocardium. Circulation. 1990;82:1034-1038.

Hintringer F, et al., Prediction of atrioventricular block during radiofrequency ablation of the slow pathway of the atrioventricular node. Circulation. 1995;92:3490-3496.

Yong Ji S, et al., Phrenic Nerve Injury: An Underrecognized and Potentially Preventable Complication of Pulmonary Vein Isolation Using a Wide-Area Circumferential Ablation Approach. J Cardiovasc Electrophysiol. 2013.

Killu Am, et al., Atypical Complications Encountered with Epicardial Electrophysiological Procedures. Heart Rhythm. 2013;10:1613-1621.

* cited by examiner

| Time (s) | 0 | 10 | 20 | 30 | 40 | 50 | 60 |
|---|---|---|---|---|---|---|---|
| PIFA 8mm Catheter 3mm | 37.5±0.3 | 50.8±6.1 | 58.7±7.6 | 63.8±9.2 | 67.4±10.4 | 70.3±11.5 | 72.4±12.0 |
| Standard 8mm Catheter 3mm | 37.5±0.5 | 42.3±2.5 | 46.2±3.6 | 48.9±4.1 | 50.7±4.3 | 52.2±4.5 | 53.3±4.5 |
| PIFA vs. STD 3mm p - value | | $p < 0.001$ | $p < 0.001$ | $p < 0.001$ | $p < 0.001$ | $p < 0.001$ | $p < 0.001$ |

| Time (s) | 0 | 10 | 20 | 30 | 40 | 50 | 60 |
|---|---|---|---|---|---|---|---|
| PIFA 8mm Catheter 5mm | 37.5±0.5 | 42.1±2.2 | 47.6±3.9 | 51.8±4.9 | 55.1±5.8 | 57.8±6.7 | 60.1±7.4 |
| Standard 8mm Catheter 5mm | 37.5±0.4 | 39.6±1.0 | 42.2±2.0 | 44.4±2.6 | 46.3±3.0 | 47.8±3.3 | 49.1±3.5 |
| PIFA vs. STD 5mm p - value | | $p = 0.003$ | $p = 0.001$ | $p < 0.001$ | $p < 0.001$ | $p < 0.001$ | $p < 0.001$ |

| Time (s) | 0 | 10 | 20 | 30 | 40 | 50 | 60 |
|---|---|---|---|---|---|---|---|
| PIFA irrigated 3mm | 37.2±0.6 | 40.5±3.3 | 52.5±8.7 | 60.1±9.7 | 65.1±10.1 | 68.4±9.9 | 70.7±9.6 |
| Standard irrigated 3mm | 37.4±0.4 | 38.9±0.9 | 44.8±3.4 | 48.8±4.1 | 51.6±4.3 | 53.6±4.4 | 55.1±4.5 |
| PIFA vs. STD 3mm p value | | p = 0.053 | p < 0.001 | p < 0.001 | p < 0.001 | p < 0.001 | p < 0.001 |

| Time (s) | 0 | 10 | 20 | 30 | 40 | 50 | 60 |
|---|---|---|---|---|---|---|---|
| PIFA irrigated 5mm | 37.1±0.7 | 38.5±1.4 | 45.0±5.7 | 50.5±7.2 | 54.8±8.0 | 58.1±8.5 | 60.5±8.7 |
| Standard irrigated 5mm | 37.4±0.4 | 38.2±0.5 | 41.8±2.2 | 45.1±3.0 | 47.6±3.4 | 49.5±3.6 | 51.1±3.7 |
| PIFA vs. STD 5mm p value | | p = 0.321 | p = 0.027 | p = 0.004 | p < 0.001 | p < 0.001 | p < 0.001 |

| Time (s) | 0 | 10 | 20 | 30 | 40 | 50 | 60 |
|---|---|---|---|---|---|---|---|
| Non-insulated 1mm | 37.1±0.3 | 41.3±0.8 | 42.8±0.9 | 43.9±1.1 | 44.6±1.2 | 45.2±1.3 | 45.7±1.4 |
| Insulated 1mm | 37.0±0.1 | 37.9±0.3 | 38.4±0.5 | 38.7±0.6 | 38.8±0.7 | 39.0±0.8 | 39.0±0.8 |
| Non-insulated vs Insulated 1mm p value | | $p<0.001$ | $p<0.001$ | $p<0.001$ | $p<0.001$ | $p<0.001$ | $p<0.001$ |
| Non-insulated 2mm | 37.1±0.1 | 38.3±0.3 | 38.9±0.4 | 39.4±0.5 | 39.7±0.6 | 40.0±0.6 | 40.2±0.7 |
| Insulated 2mm | 37.0±0.2 | 37.6±0.2 | 38.1±0.4 | 38.5±0.5 | 38.7±0.6 | 38.9±0.7 | 39.0±0.7 |
| Non-insulated vs Insulated 2mm p value | | $p<0.001$ | $p<0.001$ | $p<0.001$ | $p<0.001$ | $p<0.001$ | $p<0.001$ |
| Non-insulated 4mm | 37.2±0.1 | 37.4±0.1 | 37.5±0.1 | 37.6±0.1 | 37.6±0.1 | 37.7±0.1 | 37.7±0.1 |
| Insulated 4mm | 37.0±0.1 | 37.3±0.1 | 37.4±0.1 | 37.5±0.2 | 37.6±0.2 | 37.7±0.2 | 37.7±0.3 |
| Non-insulated vs Insulated 4mm p value | | $p = 0.02$ | $p = 0.03$ | $p = 0.14$ | $p = 0.34$ | $p = 0.60$ | $p = 0.65$ |

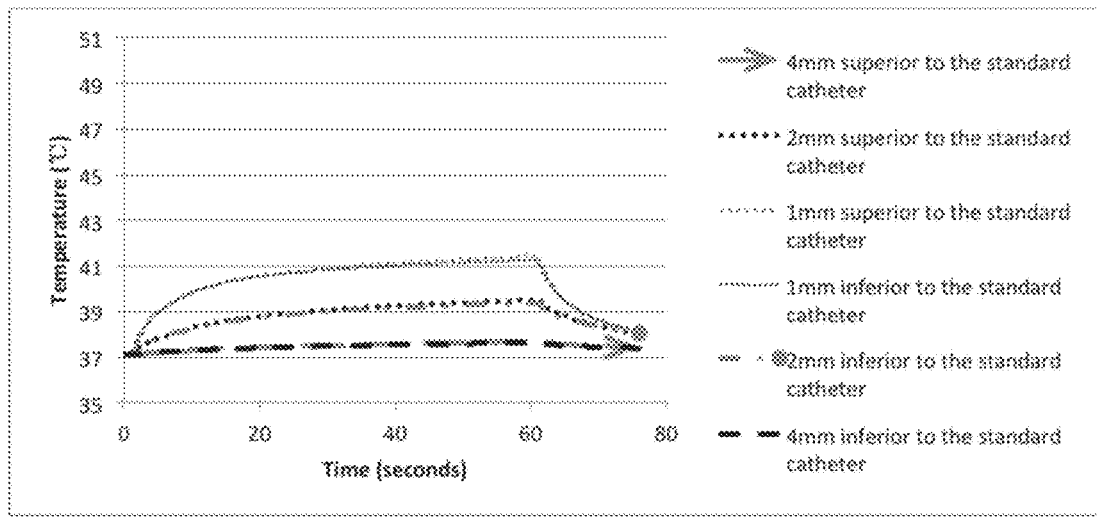

| Time (s) | 0 | 10 | 20 | 30 | 40 | 50 | 60 |
|---|---|---|---|---|---|---|---|
| 1mm superior to the standard catheter | 37.0±0.2 | 39.8±0.8 | 40.5±1.0 | 40.9±1.2 | 41.1±1.2 | 41.3±1.3 | 41.4±1.3 |
| 1mm inferior to the standard catheter | 37.0±0.1 | 39.8±0.8 | 40.5±0.9 | 40.8±1.0 | 41.0±1.1 | 41.2±1.1 | 41.3±1.2 |
| Superior vs. inferior 1mm p - value | p = 0.38 | p = 0.94 | p = 1.00 | p = 0.90 | p = 0.83 | p = 0.74 | p = 0.69 |
| 2mm superior to the standard catheter | 37.0±0.1 | 38.2±0.4 | 38.7±0.5 | 39.0±0.6 | 39.2±0.6 | 39.4±0.6 | 39.5±0.7 |
| 2mm inferior to the standard catheter | 37.1±0.1 | 38.2±0.5 | 38.7±0.6 | 39.0±0.7 | 39.1±0.7 | 39.3±0.7 | 39.4±0.8 |
| Superior vs. inferior 2mm p - value | p = 0.19 | p = 0.94 | p = 0.87 | p = 0.82 | p = 0.71 | p = 0.72 | p = 0.68 |
| 4mm superior to the standard catheter | 37.0±0.2 | 37.3±0.2 | 37.4±0.2 | 37.5±0.2 | 37.6±0.3 | 37.6±0.3 | 37.7±0.3 |
| 4mm inferior to the standard catheter | 37.1±0.1 | 37.3±0.1 | 37.4±0.2 | 37.5±0.3 | 37.5±0.3 | 37.6±0.3 | 37.6±0.3 |
| Superior vs. inferior 4mm p - value | p = 0.22 | p = 0.59 | p = 0.93 | p = 0.78 | p = 0.68 | p = 0.67 | p = 0.56 |

*FIG. 4B*

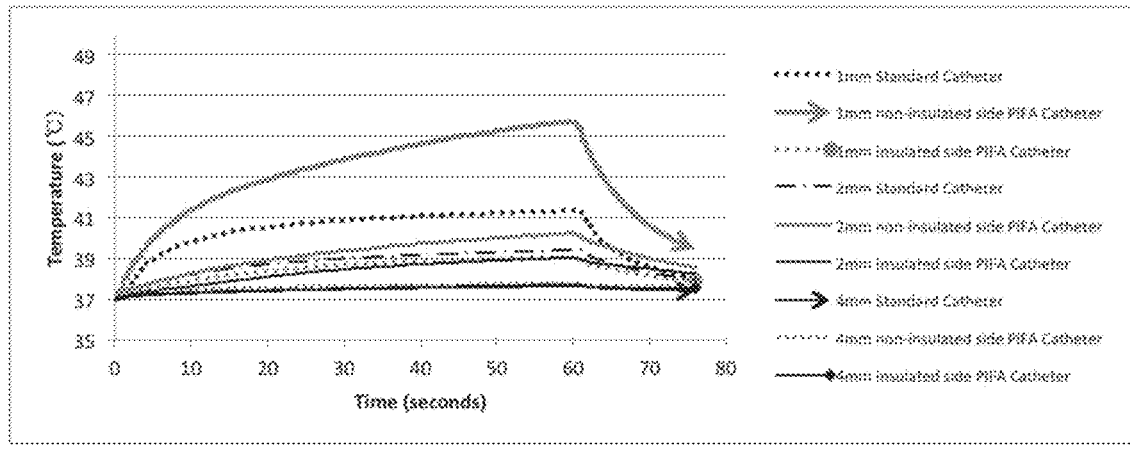

| Time (s) | 0 | 10 | 20 | 30 | 40 | 50 | 60 |
|---|---|---|---|---|---|---|---|
| Standard (STD) 1mm | 37.0±0.1 | 39.8±0.8 | 40.5±1.0 | 40.9±1.1 | 41.0±1.1 | 41.2±1.2 | 41.3±1.3 |
| Non-insulated 1mm | 37.1±0.3 | 41.3±0.8 | 42.8±0.9 | 43.9±1.1 | 44.6±1.2 | 45.2±1.3 | 45.7±1.4 |
| Non-insulated vs STD 1mm p value | | p < 0.001 | p < 0.001 | p < 0.001 | p < 0.001 | p < 0.001 | p < 0.001 |
| Insulated 1mm | 37.0±0.1 | 37.9±0.3 | 38.4±0.5 | 38.7±0.6 | 38.8±0.7 | 39.0±0.8 | 39.0±0.8 |
| Insulated vs STD 1mm p value | | p < 0.001 | p < 0.001 | p < 0.001 | p < 0.001 | p < 0.001 | p < 0.001 |
| | | | | | | | |
| STD 2mm | 37.0±0.1 | 38.2±0.4 | 38.7±0.6 | 39.0±0.6 | 39.2±0.7 | 39.3±0.7 | 39.4±0.7 |
| Non-insulated 2mm | 37.1±0.1 | 38.3±0.3 | 38.9±0.4 | 39.4±0.5 | 39.7±0.6 | 40.0±0.6 | 40.2±0.7 |
| Non-insulated vs STD 1mm p value | | p = 0.613 | p = 0.148 | p = 0.023 | p = 0.003 | p = 0.001 | p < 0.001 |
| Insulated 2mm | 37.0±0.2 | 37.6±0.2 | 38.1±0.4 | 38.5±0.5 | 38.7±0.6 | 38.9±0.7 | 39.0±0.7 |
| Insulated vs STD 2mm p value | | p < 0.001 | p < 0.001 | p = 0.002 | p = 0.011 | p = 0.039 | p = 0.064 |
| | | | | | | | |
| STD 4mm | 37.1±0.1 | 37.3±0.1 | 37.4±0.2 | 37.5±0.2 | 37.6±0.3 | 37.6±0.3 | 37.6±0.3 |
| Non-insulated 4mm | 37.2±0.1 | 37.4±0.1 | 37.5±0.1 | 37.6±0.1 | 37.6±0.1 | 37.7±0.1 | 37.7±0.1 |
| Non-insulated vs STD 4mm p value | | p < 0.001 | p = 0.003 | p = 0.017 | p = 0.066 | p = 0.066 | p = 0.084 |
| Insulated 4mm | 37.0±0.1 | 37.3±0.1 | 37.4±0.1 | 37.5±0.2 | 37.6±0.2 | 37.7±0.2 | 37.7±0.3 |
| Insulated vs STD 4mm p value | | p = 0.272 | p = 0.646 | p = 0.543 | p = 0.509 | p = 0.381 | p = 0.414 |

*FIG. 4C*

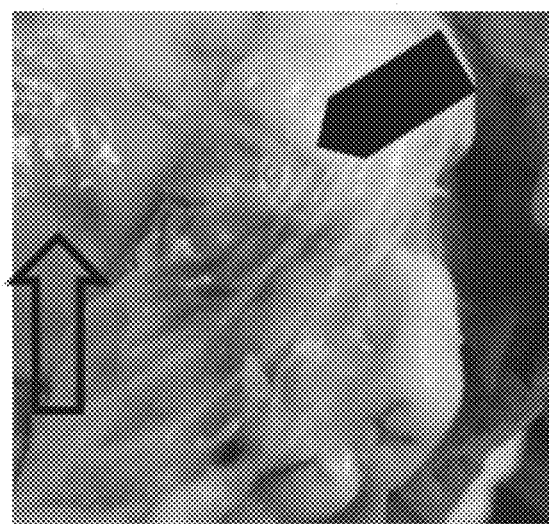 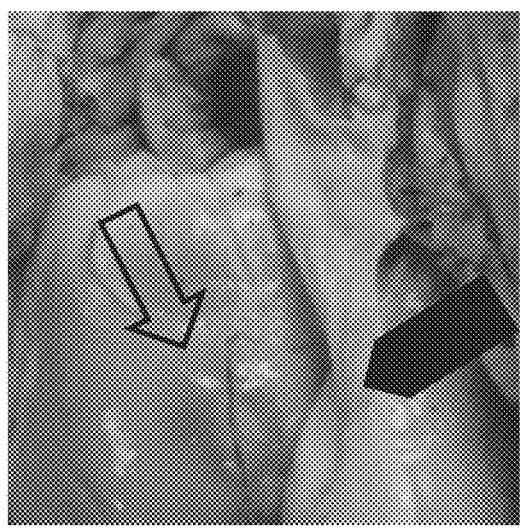
(A)            (B)
FIG. 6

| Time (s) | 0 | 10 | 20 | 30 | 40 | 50 | 60 |
|---|---|---|---|---|---|---|---|
| Non-insulated 1mm | 37.2±0.1 | 40.1±1.3 | 40.9±1.8 | 41.3±2.0 | 41.6±2.1 | 41.9±2.3 | 42.1±2.4 |
| Insulated 1mm | 37.1±0.1 | 37.7±0.3 | 38.0±0.4 | 38.1±0.5 | 38.3±0.5 | 38.3±0.6 | 38.4±0.6 |
| Non-insulated vs Insulated 1mm p value | | $p < 0.001$ | $p < 0.001$ | $p < 0.001$ | $p < 0.001$ | $p < 0.001$ | $p < 0.001$ |
| Non-insulated 2mm | 37.2±0.03 | 38.4±0.3 | 38.9±0.4 | 39.2±0.5 | 39.4±0.6 | 39.6±0.6 | 39.7±0.7 |
| Insulated 2mm | 37.1±0.1 | 37.2±0.2 | 37.3±0.2 | 37.4±0.2 | 37.5±0.3 | 37.5±0.3 | 37.5±0.3 |
| Non-insulated vs Insulated 2mm p value | | $p < 0.001$ | $p < 0.001$ | $p < 0.001$ | $p < 0.001$ | $p < 0.001$ | $p < 0.001$ |
| Non-insulated 4mm | 37.2±0.04 | 37.5±0.2 | 37.7±0.2 | 37.7±0.3 | 37.8±0.3 | 37.9±0.3 | 37.9±0.3 |
| Insulated 4mm | 37.2±0.1 | 37.3±0.1 | 37.3±0.1 | 37.3±0.1 | 37.4±0.1 | 37.4±0.1 | 37.4±0.2 |
| Non-insulated vs Insulated 4mm p value | | $p < 0.001$ | $p < 0.001$ | $p < 0.001$ | $p < 0.001$ | $p < 0.001$ | $p < 0.001$ |

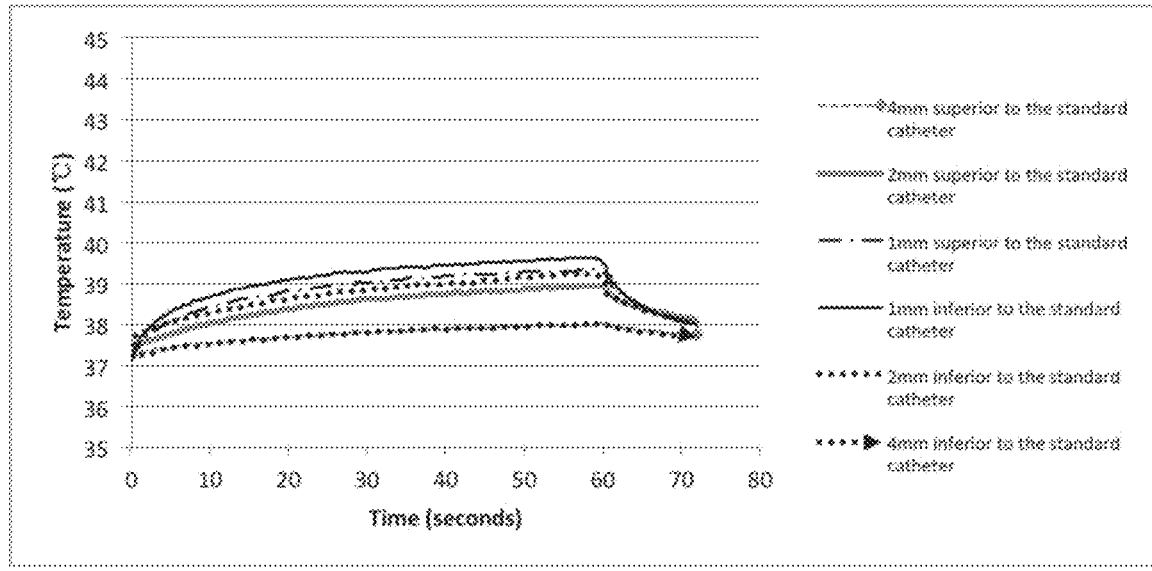

| Time (s) | 0 | 10 | 20 | 30 | 40 | 50 | 60 |
|---|---|---|---|---|---|---|---|
| 1mm superior to the standard catheter | 37.2±0.2 | 38.4±0.5 | 38.8±0.7 | 39.0±0.9 | 39.2±1.0 | 39.3±1.0 | 39.3±1.2 |
| 1mm inferior to the standard catheter | 37.3±0.4 | 38.6±0.8 | 39.1±1.0 | 39.3±1.2 | 39.4±1.2 | 39.6±1.3 | 39.5±1.2 |
| superior vs. inferior 1mm p - value | p = 0.67 | p = 0.55 | p = 0.37 | p = 0.72 | p = 0.83 | p = 0.48 | p = 0.84 |
| 2mm superior to the standard catheter | 37.3±0.3 | 38.0±0.2 | 38.4±0.2 | 38.6±0.3 | 38.7±0.3 | 38.9±0.3 | 38.9±0.4 |
| 2mm inferior to the standard catheter | 37.5±0.6 | 38.3±0.5 | 38.6±0.6 | 38.8±0.7 | 39.0±0.7 | 39.1±0.8 | 39.0±0.6 |
| superior vs. inferior 2mm p - value | p = 0.30 | p = 0.17 | p = 0.12 | p = 0.38 | p = 0.38 | p = 0.17 | p = 0.70 |
| 4mm superior to the standard catheter | 37.2±0.2 | 37.5±0.2 | 37.7±0.3 | 37.8±0.3 | 37.9±0.3 | 37.9±0.3 | 38.0±0.3 |
| 4mm inferior to the standard catheter | 37.2±0.2 | 37.5±0.2 | 37.7±0.2 | 37.8±0.3 | 37.9±0.3 | 38.0±0.3 | 38.0±0.3 |
| superior vs. inferior 4mm p - value | p = 0.47 | p = 0.98 | p = 0.85 | p = 0.60 | p = 0.89 | p = 0.78 | p = 0.86 |

*FIG. 7B*

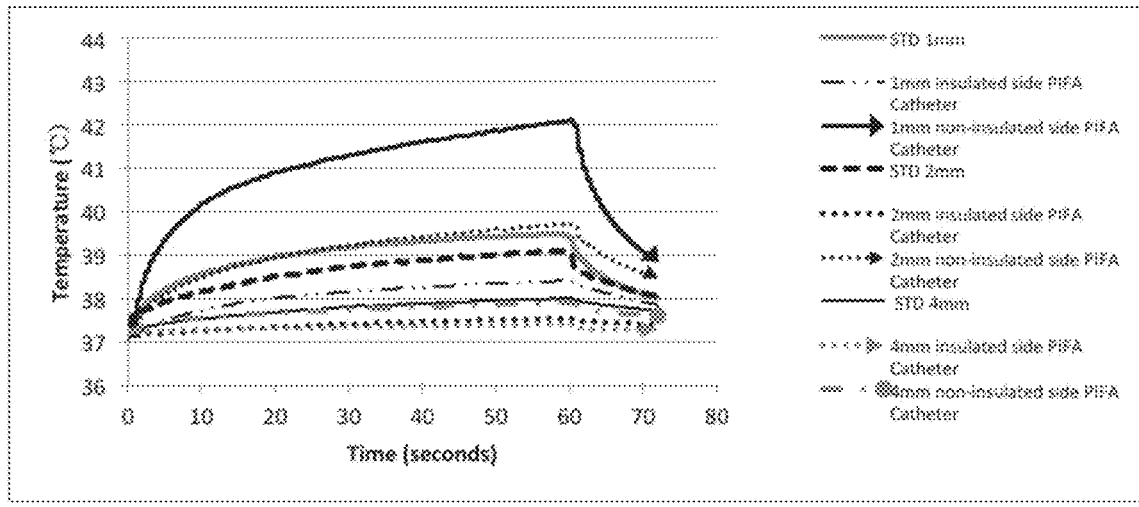

| Time (s) | 0 | 10 | 20 | 30 | 40 | 50 | 60 |
|---|---|---|---|---|---|---|---|
| Standard (STD) 1mm | 37.2±0.3 | 38.5±0.7 | 38.9±0.9 | 39.2±1 | 39.3±1.1 | 39.4±1.2 | 39.4±1.2 |
| Non-insulated 1mm | 37.2±0.1 | 40.1±1.3 | 40.9±1.8 | 41.3±2.0 | 41.6±2.1 | 41.9±2.3 | 42.1±2.4 |
| Non-insulated vs. STD 1mm p value | | $p < 0.001$ | $p < 0.001$ | $p < 0.001$ | $p < 0.001$ | $p < 0.001$ | $p < 0.001$ |
| Insulated 1mm | 37.1±0.1 | 37.7±0.3 | 38.0±0.4 | 38.1±0.5 | 38.3±0.5 | 38.3±0.6 | 38.4±0.6 |
| Insulated vs. STD 1mm p value | | $p < 0.001$ | $p < 0.001$ | $p < 0.001$ | $p < 0.001$ | $p < 0.001$ | $p < 0.001$ |
| STD 2mm | 37.4±0.5 | 38.1±0.4 | 38.5±0.5 | 38.7±0.5 | 38.9±0.6 | 39.0±0.6 | 39.0±0.5 |
| Non-insulated 2mm | 37.2±0.03 | 38.4±0.3 | 38.9±0.4 | 39.2±0.5 | 39.4±0.6 | 39.6±0.6 | 39.7±0.7 |
| Non-insulated vs. STD 2mm p value | | $p = 0.006$ | $p = 0.005$ | $p = 0.006$ | $p = 0.005$ | $p = 0.006$ | $p < 0.001$ |
| Insulated 2mm | 37.1±0.1 | 37.2±0.2 | 37.3±0.2 | 37.4±0.2 | 37.5±0.3 | 37.5±0.3 | 37.5±0.3 |
| Insulated vs. STD 2mm p value | | $p < 0.001$ | $p < 0.001$ | $p < 0.001$ | $p < 0.001$ | $p < 0.001$ | $p < 0.001$ |
| STD 4mm | 37.2±0.2 | 37.5±0.2 | 37.7±0.2 | 37.8±0.3 | 37.9±0.3 | 37.9±0.3 | 38.0±0.3 |
| Non-insulated 4mm | 37.2±0.04 | 37.5±0.2 | 37.7±0.2 | 37.7±0.3 | 37.8±0.3 | 37.9±0.3 | 37.9±0.3 |
| Non-insulated vs. STD 4mm p value | | $p = 0.576$ | $p = 0.860$ | $p = 0.592$ | $p = 0.452$ | $p = 0.364$ | $p = 0.346$ |
| Insulated 4mm | 37.2±0.1 | 37.3±0.1 | 37.3±0.1 | 37.3±0.1 | 37.4±0.1 | 37.4±0.1 | 37.4±0.2 |
| Insulated vs. STD 4mm p value | | $p < 0.001$ | $p < 0.001$ | $p < 0.001$ | $p < 0.001$ | $p < 0.001$ | $p < 0.001$ |

*FIG. 7C*

| Time (s) | 0 | 10 | 20 | 30 | 40 | 50 | 60 |
|---|---|---|---|---|---|---|---|
| Non-insulated 1mm | 37.2±0.2 | 38.0±1.5 | 39.7±2.2 | 40.2±2.2 | 40.5±2.4 | 40.4±2.4 | 40.5±2.3 |
| Insulated 1mm | 37.4±0.2 | 36.2±1.1 | 36.8±1.1 | 37.1±1.1 | 37.3±1.1 | 37.3±1.2 | 37.4±1.4 |
| Non-insulated vs Insulated 1mm p value | | $p < 0.001$ | $p < 0.001$ | $p < 0.001$ | $p < 0.001$ | $p < 0.001$ | $p < 0.001$ |
| Non-insulated 2mm | 37.4±0.1 | 37.3±0.8 | 37.6±0.9 | 38.0±1 | 38.3±1.0 | 38.4±1.1 | 38.6±1.3 |
| Insulated 2mm | 37.4±0.2 | 36.2±1.1 | 36.3±1.1 | 36.5±1 | 36.7±0.9 | 36.8±0.9 | 36.9±0.9 |
| Non-insulated vs Insulated 2mm p value | | $p = 0.004$ | $p < 0.001$ | $p < 0.001$ | $p < 0.001$ | $p < 0.001$ | $p < 0.001$ |
| Non-insulated 4mm | 37.5±0.1 | 37.5±0.3 | 37.6±0.6 | 37.8±0.7 | 38.0±0.7 | 38.2±0.8 | 38.3±0.8 |
| Insulated 4mm | 37.5±0.2 | 37.2±0.5 | 37.1±0.6 | 37.3±0.6 | 37.3±0.6 | 37.4±0.6 | 37.5±0.7 |
| Non-insulated vs Insulated 4mm p value | | $p = 0.039$ | $p = 0.033$ | $p = 0.022$ | $p = 0.006$ | $p = 0.006$ | $p = 0.005$ |

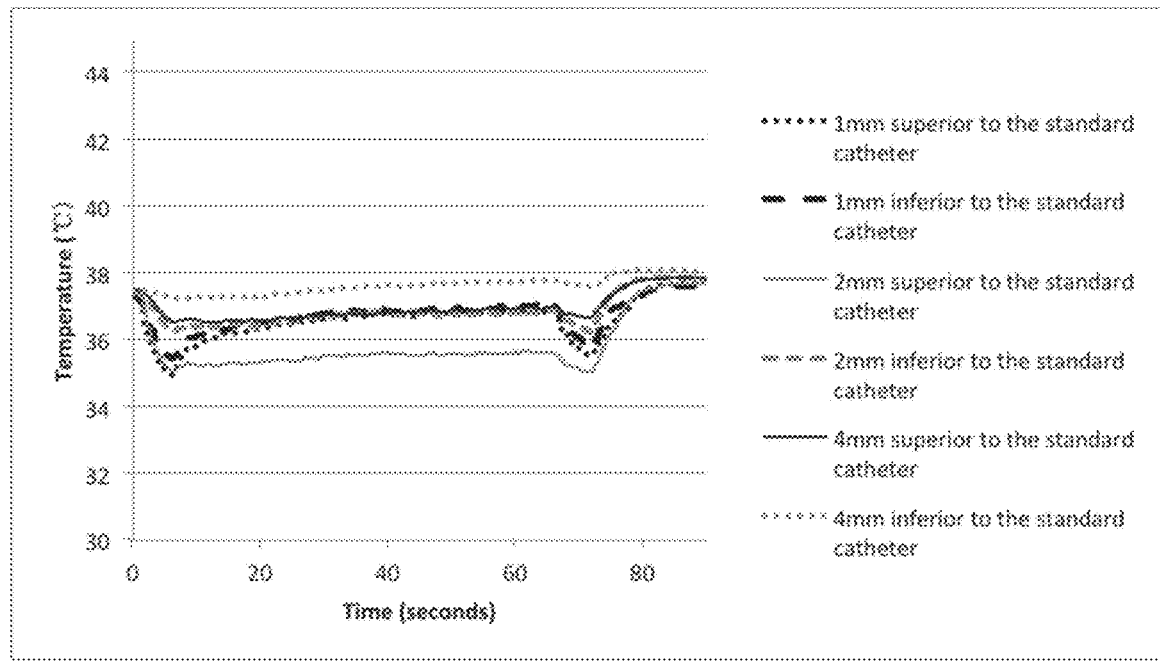

| Time (s) | 0 | 10 | 20 | 30 | 40 | 50 | 60 |
|---|---|---|---|---|---|---|---|
| 1mm superior to the standard catheter | 37.3±0.2 | 35.8±1.2 | 36.3±1.3 | 36.6±1.4 | 36.7±1.4 | 36.8±1.3 | 36.9±1.2 |
| 1mm inferior to the standard catheter | 37.3±0.2 | 36.0±1.8 | 36.5±1.9 | 36.8±1.9 | 36.9±2.0 | 37.0±2.1 | 37.0±2.2 |
| Superior vs. inferior 1mm p - value | | p = 0.703 | p = 0.802 | p = 0.777 | p = 0.809 | p = 0.793 | p = 0.845 |
| 2mm superior to the standard catheter | 37.4±0.2 | 35.3±1.3 | 35.3±1.3 | 35.5±1.2 | 35.6±1.2 | 35.6±1.2 | 35.6±1.2 |
| 2mm inferior to the standard catheter | 37.4±0.1 | 36.4±1.5 | 36.4±1.8 | 36.7±1.8 | 36.8±1.7 | 36.8±1.7 | 36.9±1.8 |
| Superior vs. inferior 2mm p - value | | p = 0.034 | p = 0.051 | p = 0.033 | p = 0.028 | p = 0.023 | p = 0.032 |
| 4mm superior to the standard catheter | 37.5±0.2 | 36.6±0.8 | 36.6±0.9 | 36.8±0.9 | 36.8±0.9 | 36.9±0.9 | 36.9±1.0 |
| 4mm inferior to the standard catheter | 37.5±0.1 | 37.3±0.6 | 37.3±0.9 | 37.5±0.9 | 37.6±1.0 | 37.7±1.0 | 37.8±1.1 |
| Superior vs. inferior 4mm p - value | | p = 0.009 | p = 0.027 | p = 0.025 | p = 0.019 | p = 0.020 | p = 0.026 |

*FIG. 8B*

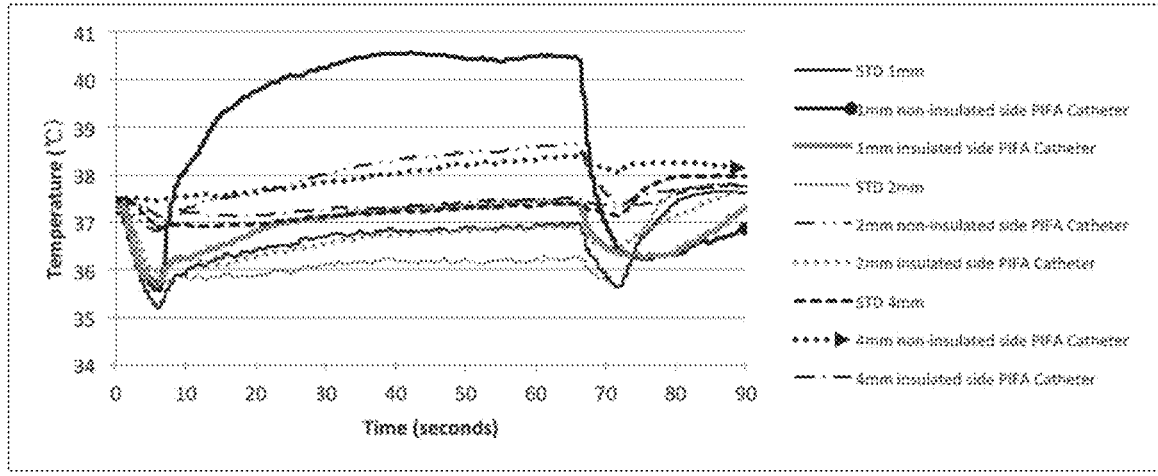

| Time (s) | 0 | 10 | 20 | 30 | 40 | 50 | 60 |
|---|---|---|---|---|---|---|---|
| STD 1mm | 37.3±0.2 | 35.9±1.5 | 36.4±1.6 | 36.7±1.7 | 36.8±1.7 | 36.9±1.7 | 36.9±1.7 |
| Non-insulated 1mm | 37.2±0.2 | 38.0±1.5 | 39.7±2.2 | 40.2±2.2 | 40.5±2.4 | 40.4±2.4 | 40.5±2.3 |
| Non-insulated vs. STD 1mm p value | | $p < 0.001$ | $p < 0.001$ | $p < 0.001$ | $p < 0.001$ | $p < 0.001$ | $p < 0.001$ |
| Insulated 1mm | 37.4±0.2 | 36.2±1.1 | 36.8±1.1 | 37.1±1.1 | 37.3±1.1 | 37.3±1.2 | 37.4±1.4 |
| Insulated vs. STD 1mm p value | | $p = 0.432$ | $p = 0.335$ | $p = 0.314$ | $p = 0.272$ | $p = 0.328$ | $p = 0.287$ |
| STD 2mm | 37.4±0.2 | 35.8±1.5 | 35.9±1.6 | 36.1±1.6 | 36.2±1.6 | 36.2±1.6 | 36.2±1.6 |
| Non-insulated 2mm | 37.4±0.1 | 37.3±0.8 | 37.6±0.9 | 38.0±1.0 | 38.3±1.0 | 38.4±1.1 | 38.6±1.3 |
| Non-insulated vs. STD 2mm p value | | $p < 0.001$ | $p < 0.001$ | $p < 0.001$ | $p < 0.001$ | $p < 0.001$ | $p < 0.001$ |
| Insulated 2mm | 37.4±0.2 | 36.2±1.1 | 36.3±1.1 | 36.5±1.0 | 36.7±0.9 | 36.8±0.9 | 36.9±0.9 |
| Insulated vs. STD 2mm p value | | $p = 0.346$ | $p = 0.339$ | $p = 0.293$ | $p = 0.162$ | $p = 0.115$ | $p = 0.081$ |
| STD 4mm | 37.5±0.2 | 37.0±0.8 | 37±1.0 | 37.1±1.0 | 37.2±1.0 | 37.3±1.1 | 37.4±1.1 |
| Non-insulated 4mm | 37.5±0.1 | 37.5±0.3 | 37.6±0.6 | 37.8±0.7 | 38.0±0.7 | 38.2±0.8 | 38.3±0.8 |
| Non-insulated vs. STD 4mm p value | | $p = 0.001$ | $p = 0.007$ | $p = 0.010$ | $p = 0.004$ | $p = 0.002$ | $p = 0.002$ |
| Insulated 4mm | 37.5±0.2 | 37.2±0.5 | 37.1±0.6 | 37.3±0.6 | 37.3±0.6 | 37.4±0.6 | 37.5±0.7 |
| Insulated vs. STD 4mm p value | | $p = 0.224$ | $p = 0.434$ | $p = 0.607$ | $p = 0.710$ | $p = 0.558$ | $p = 0.638$ |

*FIG. 8C*

Ablation lesions at 40W for a normal 4 mm catheter (A) and the insulated catheter (B). The insulated catheter delivers a more effective lesion due to its focused RF, but the insulated side has less of an ablation effect and is more protective.

Standard 4mm

Solid Tip Partially Insulated 4mm

Solid Tip Partially Insulated 4mm – SN4 for AVNRT

"Thimble" - Partially Insulated Open Irrigated 3.5 mm

Standard Solid 8 mm

Standard Solid 8 mm – effectively cooled 4 mm

Standard Solid 8 mm – effectively cooled and insulated 4 mm

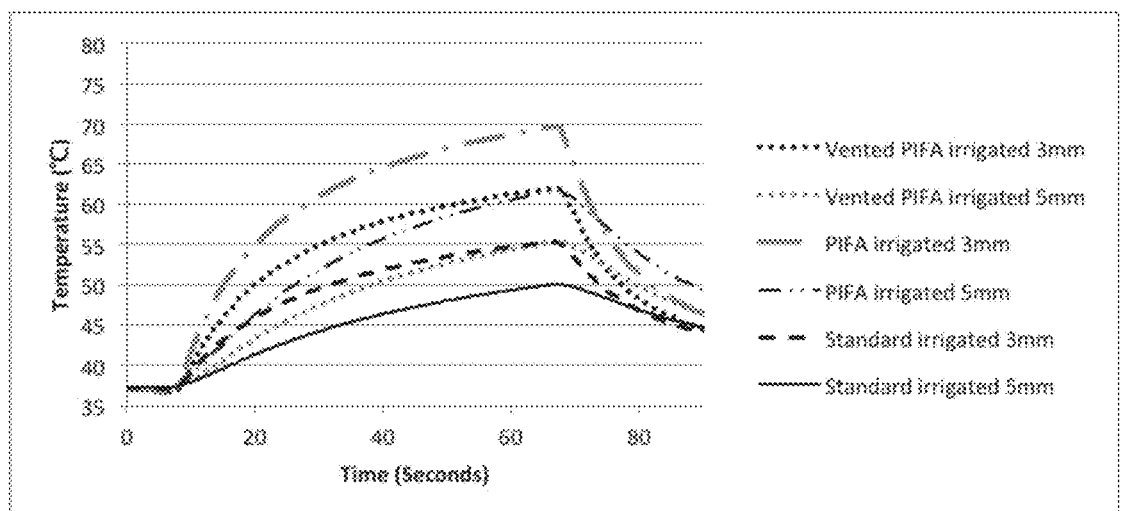

| Time (s) | 0 | 10 | 20 | 30 | 40 | 50 | 60 | 67 |
|---|---|---|---|---|---|---|---|---|
| Standard irrigated 3mm | 37.2±0.3 | 39.1±0.8 | 45.8±2.5 | 49.4±2.7 | 51.8±2.6 | 53.4±2.5 | 54.6±2.5 | 55.2±2.4 |
| Vented PIFA irrigated 3mm | 37.1±0.3 | 39.7±1.2 | 50.0±2.7 | 54.9±3.2 | 57.8±3.5 | 59.8±3.7 | 61.2±3.8 | 62.0±3.9 |
| PIFA irrigated 3mm | 36.9±0.3 | 41.5±1.8 | 54.8±3.9 | 60.8±4.1 | 64.4±4.2 | 66.8±4.3 | 68.6±4.5 | 69.6±4.5 |
| Vented PIFA vs. STD 3mm p value | p = 0.367 | p = 0.111 | p < 0.001 | p < 0.001 | p < 0.001 | p < 0.001 | p < 0.001 | p < 0.001 |
| PIFA vs. STD 3mm p value | p = 0.021 | p < 0.001 | p < 0.001 | p < 0.001 | p < 0.001 | p < 0.001 | p < 0.001 | p < 0.001 |
| Vented PIFA vs. PIFA 3mm p value | p = 0.099 | p = 0.002 | p < 0.001 | p < 0.001 | p < 0.001 | p < 0.001 | p < 0.001 | p < 0.001 |

| Time (s) | 0 | 10 | 20 | 30 | 40 | 50 | 60 | 67 |
|---|---|---|---|---|---|---|---|---|
| Standard irrigated 5mm | 37.3±0.3 | 37.9±0.4 | 41.3±1.3 | 44.2±1.8 | 46.3±2.0 | 48.0±2.1 | 49.3±2.2 | 50.0±2.2 |
| Vented PIFA irrigated 5mm | 37.3±0.3 | 38.1±0.5 | 43.2±1.5 | 47.4±2.1 | 50.4±2.4 | 52.6±2.7 | 54.3±2.9 | 55.3±3.0 |
| PIFA irrigated 5mm | 37.2±0.3 | 38.6±0.7 | 46.2±3.1 | 51.7±4.0 | 55.6±4.4 | 58.3±4.6 | 60.4±4.8 | 61.5±5.0 |
| Vented PIFA vs. STD 5mm p value | p = 0.766 | p = 0.318 | p < 0.001 | p < 0.001 | p < 0.001 | p < 0.001 | p < 0.001 | p < 0.001 |
| PIFA vs. STD 5mm p value | p = 0.292 | p = 0.001 | p < 0.001 | p < 0.001 | p < 0.001 | p < 0.001 | p < 0.001 | p < 0.001 |
| Vented PIFA vs. PIFA 5mm p value | p = 0.449 | p = 0.014 | p = 0.003 | p < 0.001 | p < 0.001 | p < 0.001 | p < 0.001 | p < 0.001 |

*FIG. 25*

PARTIALLY INSULATED FOCUSED RADIOFREQUENCY ABLATION CATHETER

CROSS-REFERENCE TO RELATED APPLICATIONS

This application claims the benefit of U.S. Provisional Application No. 62/079,992, filed Nov. 14, 2014, and U.S. Provisional Application No. 62/114,371, filed Feb. 10, 2015.

FIELD OF INVENTION

This invention relates to medical devices. More specifically, this invention relates to partially insulated radiofrequency ablation catheter tips.

BACKGROUND OF THE INVENTION

Cardiac arrhythmias comprise a major health problem; ventricular arrhythmias are the number one cause of death in the U.S. Cardiac ablation using radiofrequency (RF) energy is the standard treatment for most arrhythmias refractory to medical therapy. RF current heats tissue via resistive heating of a thin rim of tissue that is in direct contact with the ablation tip [Nath S, et al., *J Cardiovasc Electrophysiol.* 1994; 5:863-876]. Deeper tissue heating is due to passive thermal conduction from this small area of volume heating, [Haines D. *J Cardiovasc Electrophysiol.* 2004; 15:52-S11] and ablation lesion size is related to the temperature at the electrode-tissue interface, size of the ablation tip, RF duration, and tissue contact [Langberg J J, et al., *Pacing Clin Electrophysiol.* 1990; 13:1242-1248; Otomo K, et al., *J Cardiovasc Electrophysiol.* 1998; 9:47-54; Haines D E, et al., *Circulation.* 1990; 82:1034-1038].

One limitation of RF ablation is the inability to achieve durable lesions with the safe delivery of low power to myocardial tissue. Furthermore, ablation may be constrained due to anatomic considerations, such as proximity to critical structures, including the atrioventricular (AV) node, phrenic nerve, or pericardium [Hintringer F, et al., *Circulation.* 1995; 92:3490-3496; Yong Ji S, et al., *J Cardiovasc Electrophysiol.* 2013; Killu A M, et al., *Heart Rhythm.* 2013; 10:1613-1621]. In addition, when ablating myocardial tissue, only one side of the ablation catheter is adjacent to the tissue being targeted; RF from the contralateral side is either lost due to circulating blood or can potentially injure adjacent tissue.

Radiofrequency (RF) ablation has revolutionized the treatment of cardiac arrhythmias over the last couple decades. However, significant limitations remain, in terms of both safety and efficacy of RF ablation. Risks include collateral damage to vital cardiac and non-cardiac structures and unnecessary ablation of healthy tissue. Furthermore, durable and effective ablation lesions can be incomplete, particularly for challenging arrhythmias, such as atrial fibrillation and ventricular tachycardia.

All radiofrequency ablation catheters have radial symmetry at the catheter tip cylinder allowing for the delivery of RF at all sites of the catheter. However, there are many circumstances where RF energy applied in an unrestricted manner from the circumferential catheter tip cylinder results in complications due to unintended collateral injury to structures adjacent to the targeted cardiac tissue. This situation is most commonly observed during RF application near the atrioventricular node and in the epicardium. When energy is applied to tissue below the AV node, RF energy is inevitably delivered higher than what is targeted. Likewise, catheters used for the delivery of RF energy on the epicardium deliver the energy circumferentially through a metal tip. This inefficient method results in the unnecessary heating and ablation of the pericardium and often results in pericarditis (a common complication of the procedure).

What is needed to overcome these significant limitations is a catheter design that effectively delivers RF energy to the targeted tissue while avoiding collateral damage to adjacent tissue. However, in view of the art considered as a whole at the time the present invention was made, it was not obvious to those of ordinary skill in the field of this invention how the shortcomings of the prior art could be overcome.

SUMMARY OF THE INVENTION

The long-standing but heretofore unfulfilled need for is now met by a new, useful, and nonobvious invention. There is an unmet need in catheter design that allows for a more tailored approach during RF ablation in which circumferential ablation is not desired. There are many circumstances where RF energy restricted to a single side of the catheter may prevent complications due to unintended collateral injury to vital structures adjacent to the targeted cardiac tissue. This situation is most commonly observed during RF application near the atrioventricular (AV) node, in the epicardium, and near the phrenic nerve. Furthermore, a circumferential catheter may lead to unintended loss of RF to surrounding blood flow, thus decreasing the efficacy of ablation. An insulated catheter, where RF energy is concentrated to a single side, will allow for a more effective ablation at lower powers, potentially improving safety. It will also permit RF delivery deeper into tissues and is therefore useful for difficult arrhythmias arising from deep structures such as the septum, papillary muscle, and cavotricuspid isthmus.

In a first aspect the present invention provides an ablation catheter system for ablating the tissue of a body, such as cardiac tissue. The ablation catheter system includes a catheter body including a distal tip, at least one ablation electrode at the distal tip of the catheter body and an insulating layer disposed over a portion of the ablation electrode, wherein the insulating layer prevents or reduces the application of heat to tissues adjacent to the site of ablation. The distal tip of the ablation catheter can be rotatable. By making the tip and/or insulation rotatable a user can alter the orientation of the insulating layer.

The insulating layer of the first aspect can be a thermally conductive electrical insulation. In an advantageous embodiment the insulating layer can be aluminum oxide, boron nitride, aluminum oxide and boron nitride composite, silicone, vinyl, polyurethane, carbon nanotubes oriented perpendicular to the RF current, graphite embedded in thermal epoxy or diamond embedded in thermal epoxy. In a particularly advantageous embodiment the insulating layer is an aluminum oxide/boron nitride (AOBN) coating. In further advantageous embodiments the insulating layer is applied to about one-half of the surface area of the tip.

The tip of the ablation catheter system can be a non-irrigated about 4 mm RF catheter tip, non-irrigated 8 mm RF catheter tip, and an open-irrigated RF ablation catheter tip. In an advantageous embodiment the insulating layer covers the superior aspect of the catheter tip. In other words, the aspect of the tip away from the site of ablation is covered with insulating material. In another embodiment the insulating layer covers about one-half of the catheter tip.

The ablation catheter system can include one or more ports in the insulation to allow for irrigation through the insulating layer. Similarly, the ablation catheter system can employ an insulating layer that has a plurality of holes dispersed over the insulating layer thereby exposing portions of the metal ablation tip through the holes in the insulating. This allows for venting from the metal underneath the insulation.

In a second aspect the present invention provides a second ablation catheter system for ablating the tissue of a body. The ablation catheter system of the second aspect includes a catheter body including a distal tip, at least one ablation electrode at the distal tip of the catheter body, and an insulating layer disposed over a portion of the ablation electrode. The insulating layer has a plurality of holes dispersed over the insulating layer to expose portions of the metal ablation tip through the holes in the insulating layer. The insulating layer prevents or reduces the application of heat to tissues adjacent to the site of ablation.

The insulating layer of the first aspect can be a thermally conductive electrical insulation. In an advantageous embodiment the insulating layer can be aluminum oxide, boron nitride, aluminum oxide and boron nitride composite, silicone, vinyl, polyurethane, carbon nanotubes oriented perpendicular to the RF current, graphite embedded in thermal epoxy or diamond embedded in thermal epoxy. In a particularly advantageous embodiment the insulating layer is an aluminum oxide/boron nitride (AOBN) coating. In further advantageous embodiments the insulating layer is applied to about one-half of the surface area of the tip.

The tip of the ablation catheter system can be a non-irrigated about 4 mm RF catheter tip, non-irrigated 8 mm RF catheter tip, and an open-irrigated RF ablation catheter tip. In an advantageous embodiment the insulating layer covers the superior aspect of the catheter tip. In other words, the aspect of the tip away from the site of ablation is covered with insulating material. In another embodiment the insulating layer covers about one-half of the catheter tip.

The ablation catheter system can include one or more ports in the insulation to allow for irrigation through the insulating layer.

In a third aspect the present invention provides an interchangeable ablation catheter tip for a radiofrequency ablation catheter. The interchangeable ablation catheter tip includes an ablation electrode which has an insulating layer disposed over a portion of the ablation electrode. The insulating layer prevents or reduces the application of heat to tissues adjacent to the site of ablation. The interchangeable ablation catheter tip is adapted to releasably engage a distal tip of a radiofrequency catheter body, thus facilitating the exchange of catheter tips on a catheter.

In certain embodiments the tip can be a non-irrigated about 4 mm RF catheter tip, a non-irrigated 8 mm RF catheter tip, or an open-irrigated RF ablation catheter tip.

In an advantageous embodiment the insulating layer covers the superior aspect of the catheter tip. In other words, the aspect of the tip away from the site of ablation is covered with insulating material. In another embodiment the insulating layer covers about one-half of the catheter tip.

The interchangeable ablation catheter tip can include one or more ports in the insulation to allow for irrigation through the insulating layer. Similarly, the interchangeable ablation catheter tip can employ an insulating layer that has a plurality of holes dispersed over the insulating layer thereby exposing portions of the metal ablation tip through the holes in the insulating. This allows for venting from the metal underneath the insulation.

The insulating layer of the interchangeable ablation catheter tip can be a thermally conductive electrical insulation.

In an advantageous embodiment the insulating layer can be aluminum oxide, boron nitride, aluminum oxide and boron nitride composite, silicone, vinyl, polyurethane, carbon nanotubes oriented perpendicular to the RF current, graphite embedded in thermal epoxy or diamond embedded in thermal epoxy. In a particularly advantageous embodiment the insulating layer is an aluminum oxide/boron nitride (AOBN) coating.

BRIEF DESCRIPTION OF THE DRAWINGS

For a fuller understanding of the invention, reference should be made to the following detailed description, taken in connection with the accompanying drawings, in which:

In FIG. 4A, the upper thick black solid line with the arrow head is the plot of the 1 mm to the non-insulated side of the PIFA catheter. The next line, the middle dashed black line, is the plot of the 2 mm non-insulated side of the PIFA catheter. The upper, roughly coextensive black dotted line is the 1 mm insulated side of the PIFA catheter and the 2 mm insulated side of the PIFA catheter (i.e. the thinner solid black line), where the 1 mm catheter has a slightly higher temperature at 20 seconds and slightly lower temperature at 70 seconds. The lowest line(s) plotted in FIG. 4A represent the 4 mm non-insulated side of the PIFA catheter and 4 mm insulated side of the PIFA catheter. The plots are coextensive and difficult to distinguish in gray scale.

FIG. 4B is a graph illustrating the mean surface temperature dispersion at 1 mm, 2 mm, and 4 mm distances from each side (insulated, non-insulated) of a standard 4 mm catheter. In FIG. 4B only three lines are distinguishable in the gray scale plots of the six different catheters. The upper line plot represents both the 1 mm superior to the standard catheter and 1 mm inferior to the standard catheter. The middle line plot represents 2 mm superior to the standard catheter and 2 mm inferior to the standard catheter. The lower line plot represents 4 mm superior to the standard catheter and 4 mm inferior to the standard catheter.

FIG. 4C provides comparisons between the catheters as shown in FIGS. 4A and 4B.

FIG. 4C: Identification of line plots from upper to lower at the 60 second time interval: upper line=1 mm from non-insulated side of the PIFA catheter; second line=1 mm from standard catheter; third line=2 mm from non-insulated side of the PIFA catheter; fourth line=2 mm from standard catheter; fifth line=1 mm from insulated side of the PIFA catheter and 2 mm from insulated side of the PIFA catheter; lower line=4 mm from standard catheter, 4 mm from non-insulated side of the PIFA catheter and 4 mm from insulated side of the PIFA catheter.

FIG. 6 is a pair of images illustrating in vivo epicardial ablation using open irrigated standard catheter (A) and PIFA open irrigated catheter (B). In (A), the control epicardial lesion (open arrow) is adjacent to pericardium (black arrow) that appears ablated. In (B), the PIFA lesion (open arrow), although significantly larger than the control lesion, is adjacent to normal appearing pericardium (black arrow).

FIG. 7A: Mean Surface Temperature Dispersion at 1 mm, 2 mm, and 4 mm Distances From Each Side (insulated, non-insulated) of a 8 mm PIFA Catheter. Identification of line plots from upper to lower at the 60 second time interval: upper line=1 mm non-insulated side PIFA catheter; second line=2 mm non-insulated side PIFA catheter; third line=2 mm non-insulated side PIFA catheter; fourth line=4 mm insulated side PIFA catheter; fifth line (largely coextensive with fourth line)=1 mm insulated side PIFA catheter; lower line=2 mm insulated side PIFA catheter.

FIG. 7B is a graph illustrating the mean surface temperature dispersion at 1 mm, 2 mm, and 4 mm distances from each side (insulated, non-insulated) of a standard open irrigated catheter. FIG. 7B: Mean Surface Temperature Dispersion at 1 mm, 2 mm, and 4 mm Distances From Each Side of a Standard 8 mm Catheter. Identification of line plots from upper to lower at the 60 second time interval: upper line=4 mm inferior to the standard catheter; lines 2-5 (largely coextensive from 20 to 60 seconds on the graph)=1 mm superior to the standard catheter, 1 mm inferior to the standard catheter, 2 mm inferior to the standard catheter, and 4 mm superior to the standard catheter; third line=2 mm inferior to the standard catheter; fourth line=2 mm superior to the standard catheter; lower line=2 mm superior to the standard catheter.

FIG. 7C provides comparisons between the catheters as shown in FIGS. 7A and 7B. FIG. 7C: Combined Mean Surface Temperature Dispersion at 1 mm, 2 mm, and 4 mm Distances From Each Side (insulated, non-insulated) of a 8 mm PIFA Catheter and Standard (STD) 8 mm Catheter. Identification of line plots from upper to lower at the 60 second time interval: upper line=1 mm non-insulated side PIFA catheter; second line=2 mm non-insulated side PIFA catheter; third line=4 mm non-insulated side PIFA catheter; fourth line=4 mm insulated side PIFA catheter; fifth line (largely coextensive with the fourth line from 40 through 70 seconds)=standard 4 mm catheter; sixth line (largely coextensive with the fifth line from 30 through 70 seconds)=1 mm insulated side PIFA catheter; seventh line=standard 1 mm catheter; eighth line (largely coextensive with the seventh line)=2 mm insulated side PIFA catheter; ninth line=standard 2 mm catheter.

FIG. 8A: Identification of line plots from upper to lower at the 60 second time interval: upper line=1 mm non-insulated side PIFA catheter; second line=2 mm non-insulated side PIFA catheter; third line=1 mm insulated side PIFA catheter; fourth line=4 mm non-insulated side PIFA catheter; fifth line=2 mm insulated side PIFA catheter; lower line=4 mm insulated side PIFA catheter.

FIG. 8B is a graph illustrating the mean surface temperature dispersion at 1 mm, 2 mm, and 4 mm distances from each side (insulated, non-insulated) of a standard 8 mm catheter. FIG. 8B: Identification of line plots from upper to lower at the 60 second time interval: upper line=1 mm inferior to the standard catheter; second line=1 mm superior to the standard catheter; third line=2 mm inferior to the standard catheter; fourth line=2 mm superior to the standard catheter; lower line=4 mm inferior to the standard catheter and 4 mm superior to the standard catheter.

FIG. 8C provides comparisons between the catheters shown in FIGS. 7A and 7B. FIG. 8C: Identification of line plots from upper to lower at the 60 second time interval: upper line=1 mm non-insulated side PIFA catheter; second line=2 mm non-insulated side PIFA catheter; third line=standard 1 mm catheter; fourth line=standard 2 mm catheter; fifth line=1 mm insulated side PIFA catheter; sixth line=standard 4 mm catheter; seventh line (largely coextensive with sixth line)=4 mm non-insulated side PIFA catheter; eighth line=2 mm insulated side PIFA catheter; ninth line (largely coextensive with eighth line)=2 mm insulated side PIFA catheter.

FIG. 13 is an illustration of an electrically active threaded stump catheter shaft and the complementary portion of an exchangeable catheter tip that the shaft interfaces with.

FIG. 25 is a graph illustrating the mean temperature dispersion at 3 and 5 mm depths for 20 Watts using irrigated Arctic Alumina insulation, irrigated Arctic Alumina vented insulation, and control open irrigated ablation.

FIG. 28A shows an open irrigated PIFA catheter.

FIG. 28B shows an open irrigated control.

DETAILED DESCRIPTION OF THE PREFERRED EMBODIMENT

Figure 1:
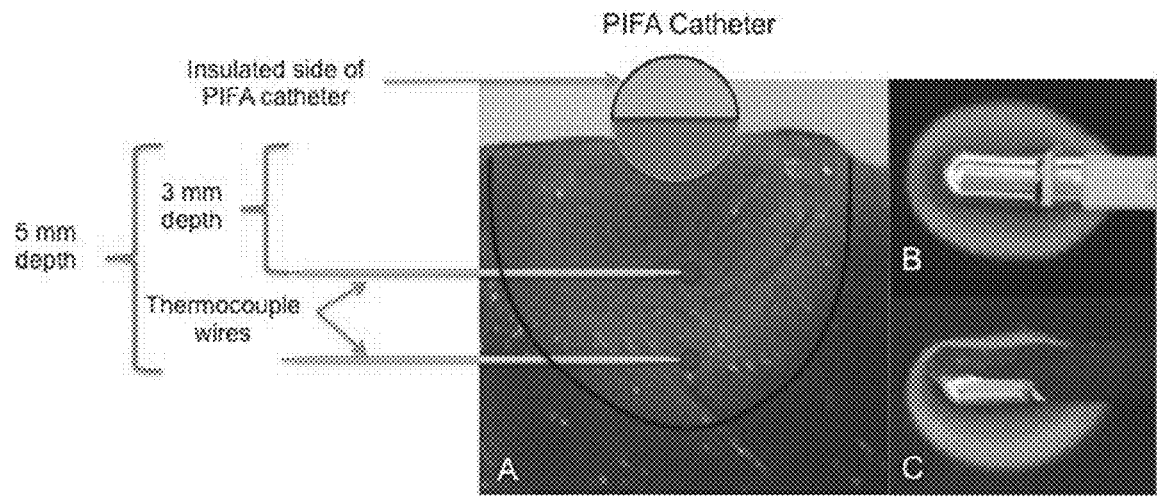
FIG. 1 is a set of three images illustrating partially insulated, focused ablation ("PIFA") catheter and thermocouple positions for depth temperature measurements. (A) shows the non-insulated side of the PIFA catheter is parallel to the myocardium. Thermocouple wires are inserted beneath the catheter tip-myocardium interface at depths of 3 and 5 mm. (B) shows shows the thermochromic pattern created with a standard catheter on heat sensitive liquid crystal paper. (C) shows the thermochromic pattern created with the PIFA catheter on heat sensitive liquid crystal paper. PIFA: partially insulated, focused ablation.

Partially insulated focused ablation (PIFA) catheters using thermally conductive materials have differential radiofrequency (RF) heating and thereby allow for tailored RF application. PIFA catheters can minimize risk of injury to critical structures, such as the phrenic nerve and AV node, during ablation. Open-irrigated, 4 mm, and 8 mm RF ablation catheters were partially insulated by coating half their surfaces with a layer of vinyl, silicone, vinyl-silicone, polyurethane, or a composite of aluminum oxide/boron nitride (AOBN). The various coatings exhibited different tip temperature performances, with silicone and AOBN displaying fewer tip temperature limitations than vinyl, vinyl-silicone, and polyurethane. Significant differences in lesion volumes and temperature-limited powers were noted for control, silicone and AOBN tips. In addition, steam pops were significantly higher for silicone but not AOBN. Compared to standard ablation, AOBN-coated PIFA catheters were able to minimize injury to the phrenic nerve and AV node. Standard ablation near the AV node caused complete heart block whereas PIFA ablation did not. RF ablation using catheter tips partially coated with a thermally conductive insulation material such as AOBN results in larger ablation lesion volumes without being limited by standard temperature controls. Partial insulation of the catheter tip is able to protect adjacent critical structures during in vivo ablation.

Effective radiofrequency ablation (RFA) can be impacted by the size of the ablation catheter tip, temperature at the electrode-tissue interface, RF duration, and tissue contact. A partially insulated catheter tip is disclosed and shown to impact ablation lesion size and shape, thereby providing additional tools to tailor the ablation to the user's needs. When insulation is partially applied to an ablation electrode, the insulation alters RF lesion geometry with minimal effect on tip temperatures. Existing catheters were modified by coating a portion of the metallic tip using a thin layer of insulation that also is thermally conductive. This allows for a more tailored cardiac ablation by improving heating under the non-insulated side of the catheter while decreasing undesired RF-mediated injury from the insulated side.

Insulation materials were investigated to demonstrate their effect on asymmetrical lesion formation while protecting the tissue adjacent to the insulated aspect of the ablation catheter tip. Using these insulation materials, we performed in vivo ablation near critical structures to demonstrate the ability of PIFA to protect these structures.

Catheter ablation of cardiac tissue with radiofrequency (RF) energy is routinely performed for the treatment of a variety of arrhythmias. All radiofrequency ablation catheters are radially symmetric at the catheter tip cylinder, thus allowing for circumferential RF. However, there is an unmet need in catheter design that allows for a more tailored approach during RF ablation in which circumferential ablation is not desired. There are many circumstances where RF energy restricted to a single side of the catheter may prevent complications due to unintended collateral injury to vital structures adjacent to the targeted cardiac tissue. This situation is most commonly observed during RF application near the AV node, in the epicardium, and near the phrenic nerve. Furthermore, a circumferential catheter tip may lead to unintended loss of RF to surrounding blood flow, thus decreasing the efficacy of ablation. An insulated catheter, where RF energy is concentrated to a single side, will allow for a more effective ablation at lower powers, potentially improving safety. It will also permit RF delivery deeper into tissues and is therefore useful for difficult arrhythmias arising from deep structures such as the septum, papillary muscle, and cavo-tricuspid isthmus.

An insulated catheter has been designed and engineered, using a silicone-vinyl coating on half the surface of a catheter tip to direct RF energy preferentially and asymmetrically to the non-insulated side of the catheter tip. Ablation studies with these PIFA catheters have met two principal objectives for clinical applicability. First, it is shown herein that the insulated sides of the PIFA catheters have decreased temperature changes and minimal tissue injury when RF ablation is delivered. Secondly, it is shown that the non-insulated sides of these catheters deliver a greater degree of tissue heating with less power, which results in larger ablation lesions.

Figure 12:
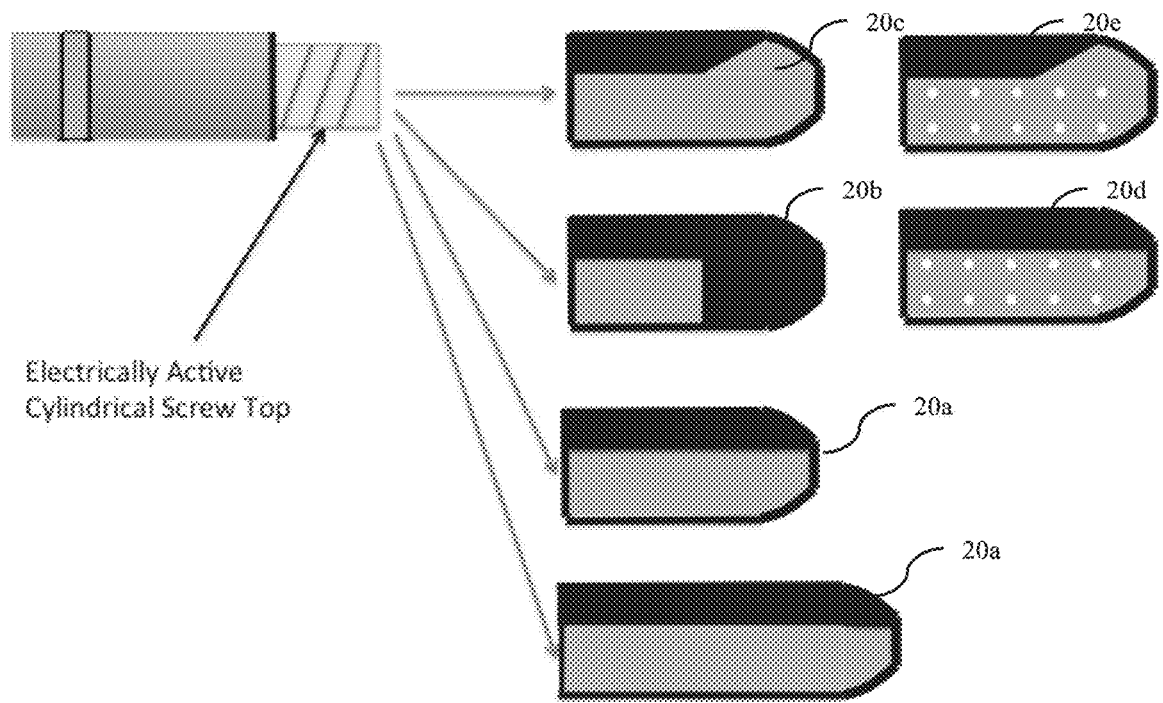
FIG. 12 is an illustration of the tip exchange for a single catheter modification.
Figure 13:
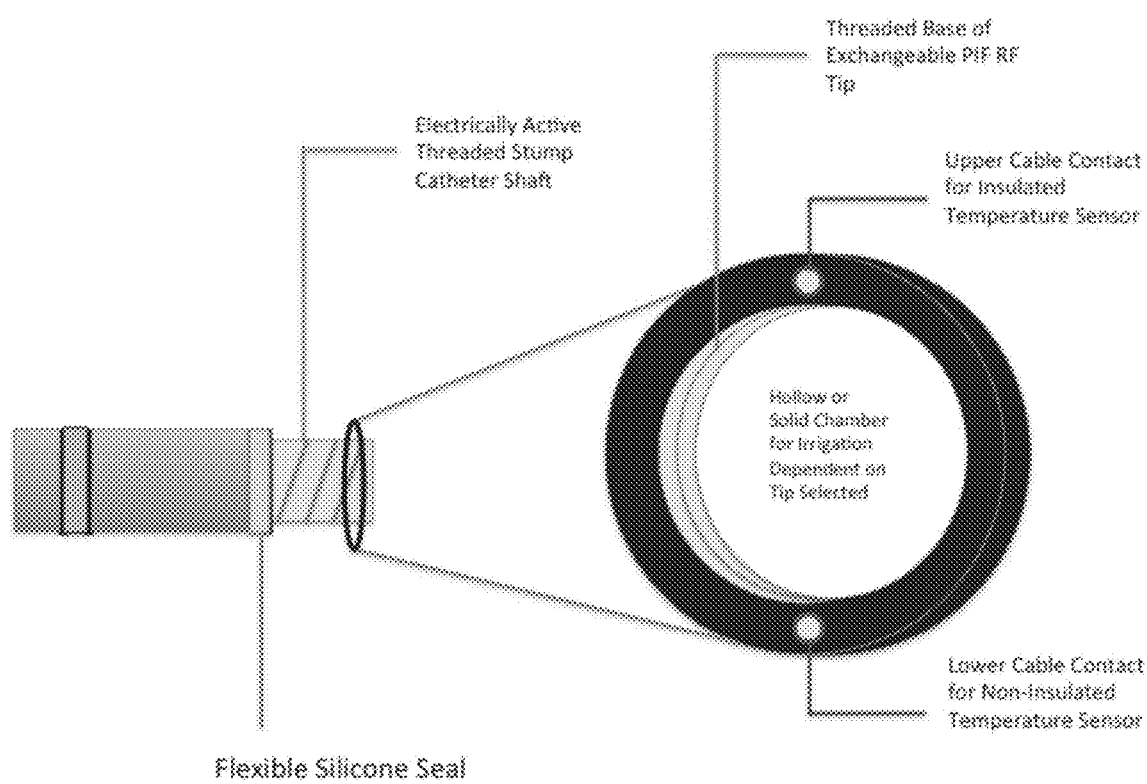
Figure 14:
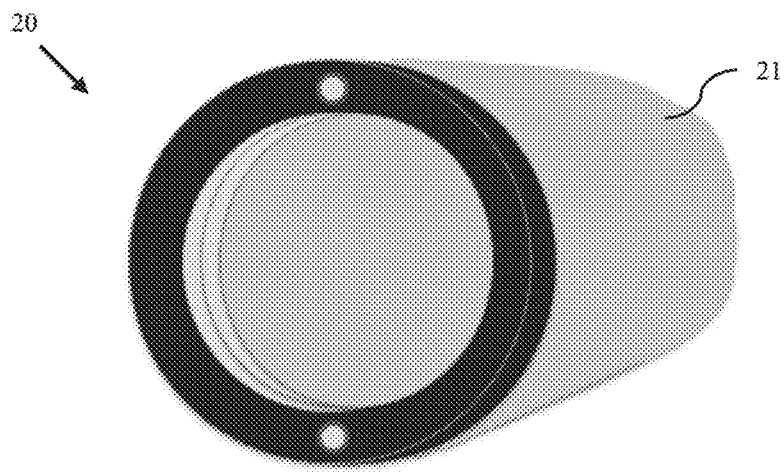
FIG. 14 is an illustration of the catheter tip interface for a standard 4 mm catheter tip.
Figure 15:
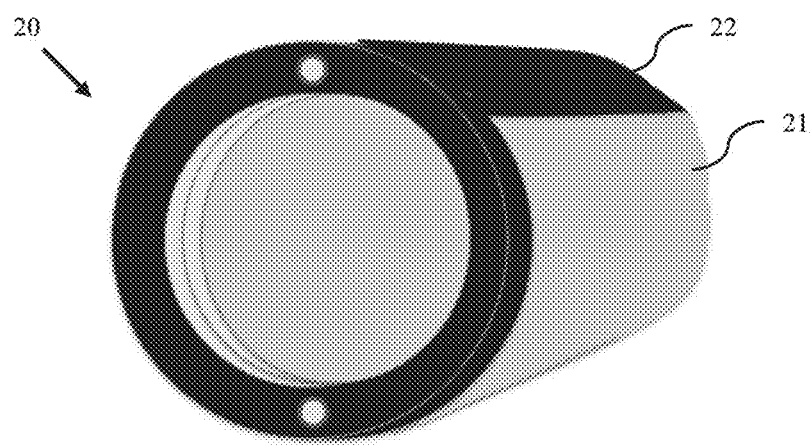
FIG. 15 is an illustration of the catheter tip interface for a solid tip partially insulated 4 mm catheter tip.
Figure 16:
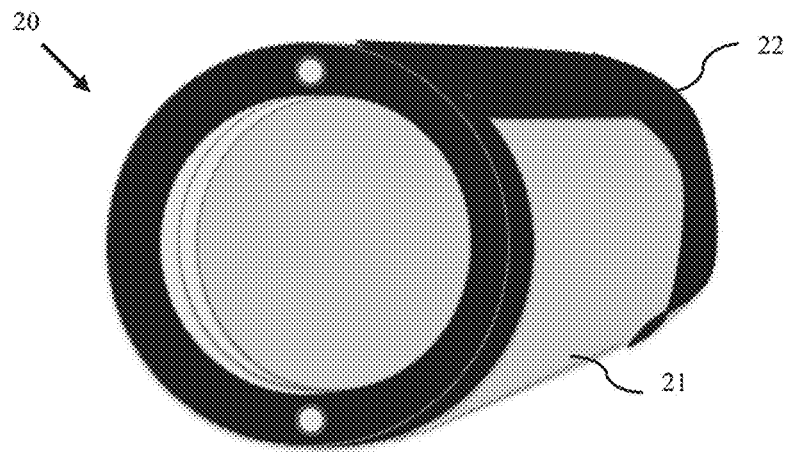
FIG. 16 is an illustration of the catheter tip interface for a solid tip partially insulated 4 mm—SN4 AVNRT catheter tip.
Figure 17:
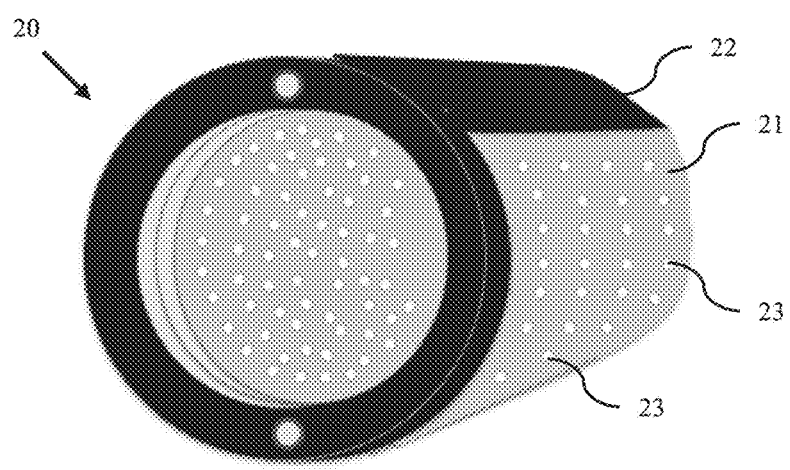
FIG. 17 is an illustration of the catheter tip interface for a "thimble" partially insulated open irrigated 3.5 mm catheter tip.
Figure 18:
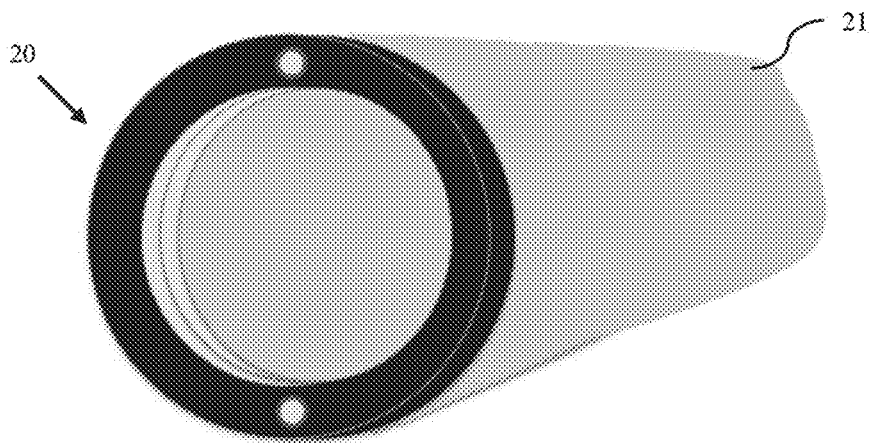
FIG. 18 is an illustration of the catheter tip interface for a standard solid 8 mm catheter tip.
Figure 19:
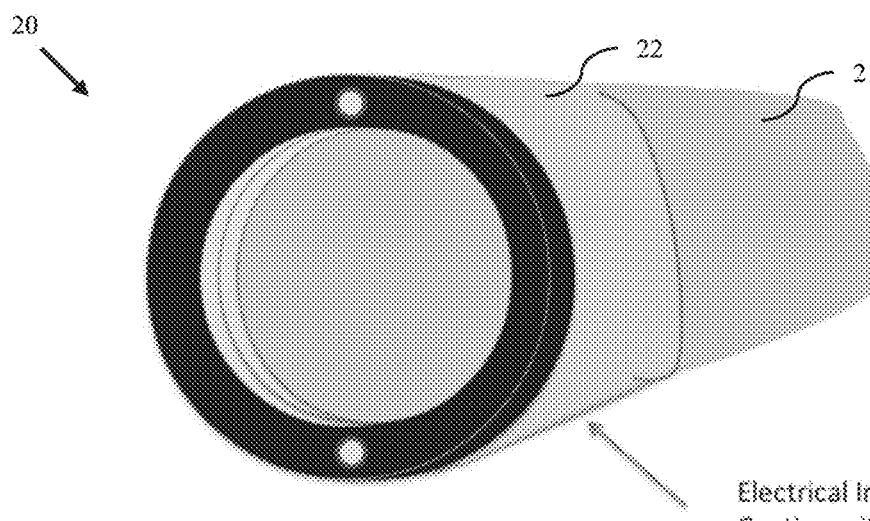
FIG. 19 is an illustration of the catheter tip interface for a standard solid 8 mm—effectively cooled 4 mm catheter tip.
Figure 20:
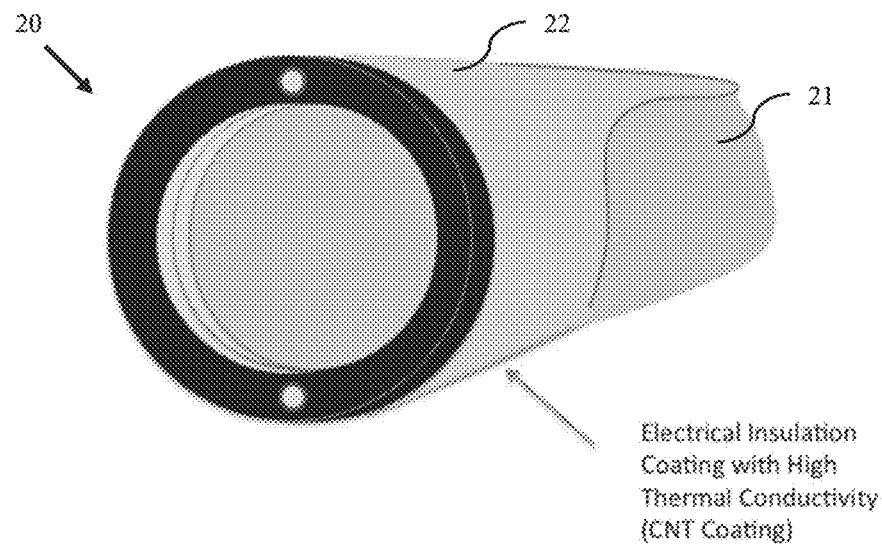
FIG. 20 is an illustration of the catheter tip interface for a standard solid 8 mm—effectively cooled and insulated 4 mm catheter tip.
Figure 23:
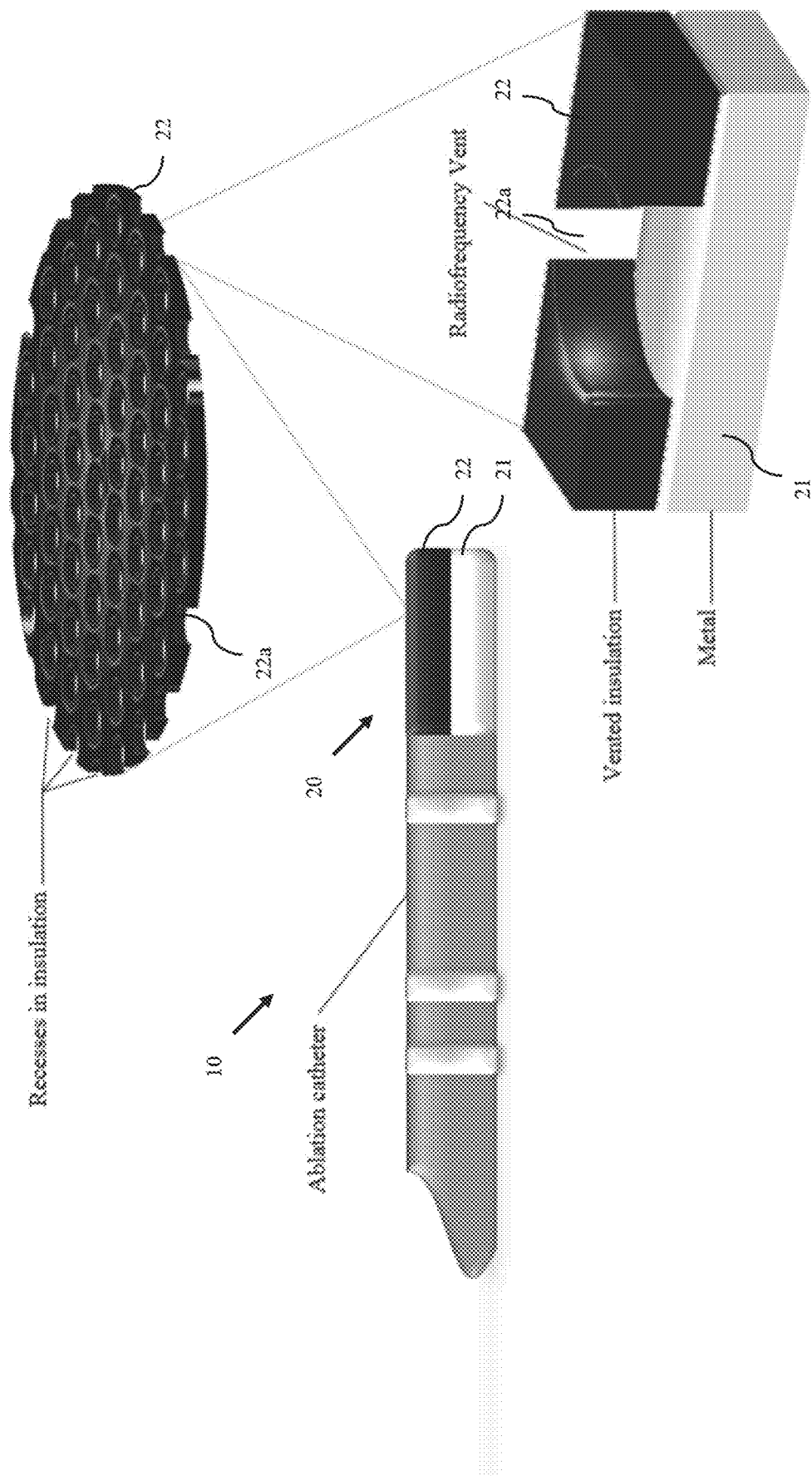
FIG. 23 is an illustration of a radiofrequency venting catheter design showing the vents in the insulation covering a portion of the tip of the catheter.

Selective electrical insulation applied to an ablation electrode to protect non-targeted myocardial tissue or structures alters RF lesion geometry with minimal effect on tip temperatures. Catheters were modified to influence RF energy delivery by coating a portion of the metallic tip using a thin layer of electrical insulation that also is thermally conductive. FIGS. 12, 15-20 and 23-24 show exemplary coating patterns. Referring to FIG. 12, a plurality of different coating patterns (20) are disclosed. Cather tips 20a and 20d have a coating over roughly one-half of the surface of the tip, with the coating applied to superior side of the tip, or the surface area that would be away from the tissue being ablated. Other coating patterns are possible. For instance, catheter tip 20b has additional insulation completely covering the distal portion of the catheter tip, while catheter tips 20c and 20e have the distal portion of the catheter tip exposed. While catheter tip 20a shows roughly 50% of the tip covered with insulation, it is contemplated that roughly 25%, 30%, 40%, 50%, 60%, 70% or 75% of the tip could be covered by insulation depending upon the application and needs of the user. FIG. 17 shows a partially insulated open irrigated 3.5 mm catheter tip having a thin layer of insulation 22 coating the metal surface 21 (having holes 23) of the catheter 20. Similarly, FIG. 23 shows an ablation catheter 10 with a catheter tip 20 having a thin layer of insulation 22 over the metal 21 of the catheter tip 20. The thin layer of insulation 22 has a plurality of holes 22a through the insulation to allow for venting from the metal 21. The vents 22a are shown in more detail in FIG. 24.

Examples of suitable coating materials include aluminum oxide, boron nitride, aluminum oxide and boron nitride composite, silicone, vinyl, polyurethane, carbon nanotubes placed perpendicular to RF current, graphite embedded in thermal epoxy and diamond embedded in thermal epoxy. These coatings would be over a tip constructed of a material such as Gold, Platinum, and Platinum-Iridium and gold and platinum alloys. The modification of the coating allows for a more tailored cardiac ablation by improving heating under the non-insulated side of the catheter while decreasing undesired RF-mediated injury from the insulated side. Partially insulated, focused ablation (PIFA) catheters were created whereby one side of various ablation catheter tips (4 mm, 8 mm, and open irrigated) was insulated with a very thin layer of thermal adhesive coating to eliminate RF conductivity on this side, while also allowing for convective cooling of the catheter tip to prevent tip temperature limitations.

A catheter has also been developed that can be easily converted from the current radially symmetric catheter tip into an insulated tip. This catheter design allows operators to exchange or convert from the current radial tip technology to a partially insulated tip. Exemplary exchangeable tips are shown in FIGS. 12, 15-17, 19-20 and 23-24. The design, which can include a rotating insulated cover, allows for either side of the catheter to be insulated, thereby maintaining the bi-directionality of the catheter. This catheter will allow clinicians to tailor their ablation strategy according to the type of cardiac tissue being targeted and depending on the arrhythmia of interest. This technology was developed using the standard 4 mm ablation catheter, but the design can easily be accommodated to the 8 mm catheter and the irrigated tip catheter. Applying the technology to irrigated tip catheters allows for even more directed and deeper ablation lesions, thereby making durable lesions for treating a variety of cardiac arrhythmias, including atrial fibrillation and ventricular tachycardia. In a first embodiment the insulated cover is in a fixed orientation with respect to the catheter tip, but further embodiments include a rotating insulated cap around the ablation catheter tip. Use of a rotating insulated cap around the ablation catheter tip allows the use of all sides of the ablation catheter, with the operators tailoring their partial insulation in the direction that they prefer. This partially insulated, rotating cap can be applied to the standard 4 mm catheter, as well as the 8 mm catheter and an irrigated tip catheter.

Figure 21:
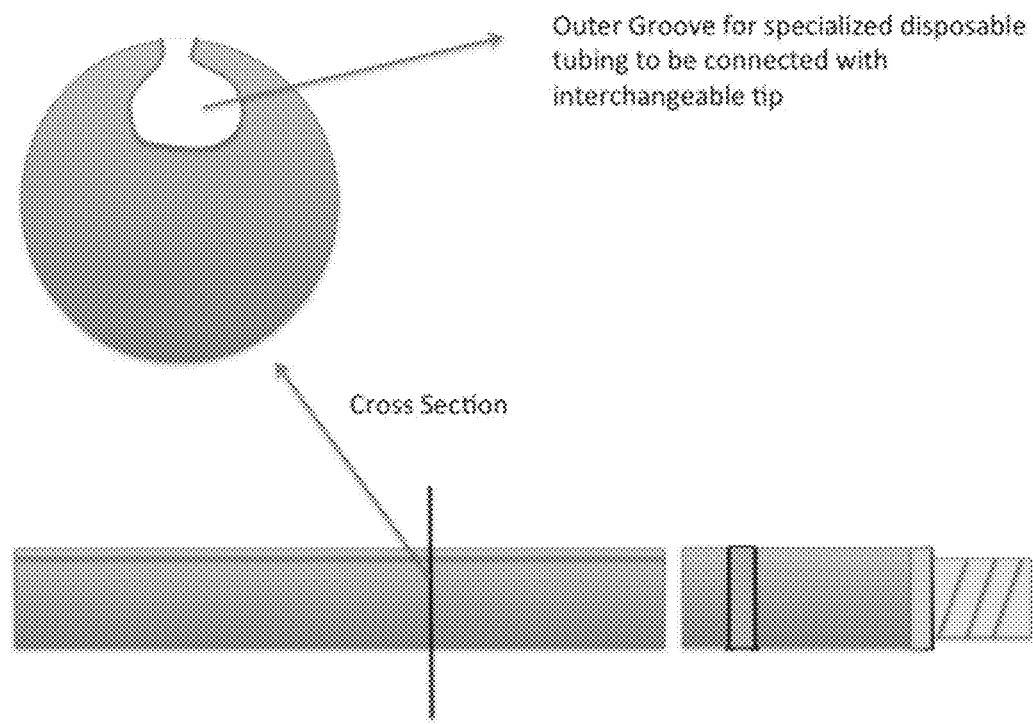
FIG. 21 is an illustration of the catheter shaft designed to accept specialized disposable tubing for irrigation.
Figure 22:
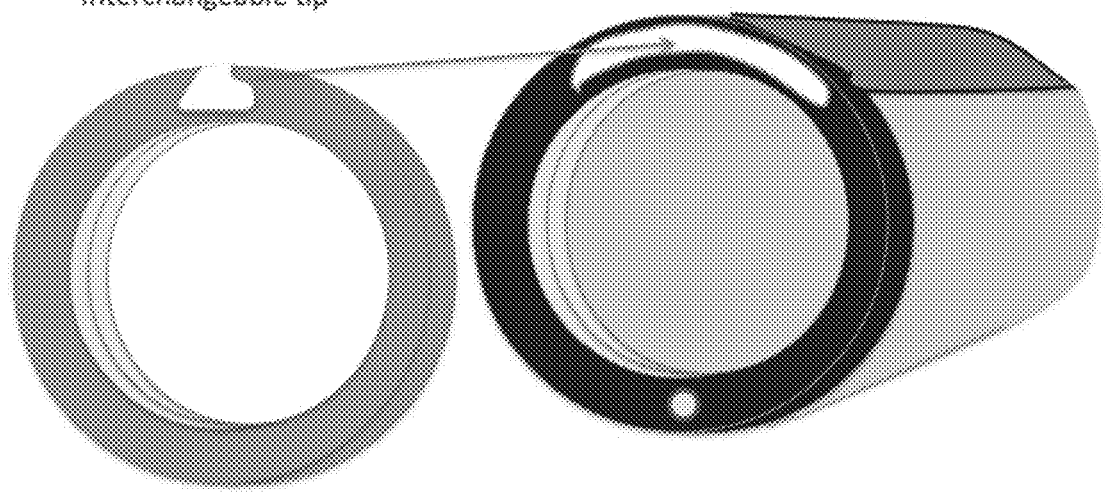
FIG. 22 is an illustration of a solid tip partially insulated and with external irrigation tubing design.

External irrigation is also contemplated. There may be concerns over recycling of lumen catheters. If irrigation tubing is moved to the outside of a catheter tip, it could also serve as insulation. FIGS. 21 and 22 disclose examples of tips with external irrigation tubing.

Additional interchangeable tips are also contemplated. These include:
   0.5 mm fine mapping tip
   Solid 4 mm with different regional insulation patterns (SN 1, SN 2, SN 3, SN 4 (AVNRT))
   Open Irrigated 3.5 mm ("Thimble")
   Open Irrigated 3.5 mm ("Thimble") different regional insulation patterns
   Repeat on the 8 mm In addition, the tip designs proposed herein can be applied to the following tip types: peanut, tapered, deformable "Blob" tip, CNT coated tip, gold or copper tip, needle tip and proximally coated 10 mm tip (electrical insulation with high thermal conductivity).

Tailored and facilitated RF ablation is paramount and is an unmet need in ablation technology. Different areas of the heart have diverse physical properties and react differently to ablation. Currently, RF ablation catheters all have the same design, with their inherent limitations, and one catheter tip design is not meant to treat all different types of tissue or arrhythmia. The only "tailoring" that can be currently performed with these catheters is to manually orient them differently or to titrate the amount of energy being delivered. The development of an insulated cover will allow for another dimension of tailoring, making ablation safer, while at the same time more effective. This technology has the potential for altering the practice of an entire field of therapeutics with a large demand of services in a high volume of patients.

This catheter could be considered for any catheter ablation procedure where focused ablation and/or tailored protective insulation are preferred. The arrhythmias that may be treated using this catheter include atrial flutter, AV nodal reentrant tachycardia, supraventricular tachycardia, atrial fibrillation, and ventricular tachycardia.

Example 1—Materials and Methods

Ex-Vivo Model

The experimental protocols employed herein have been approved by the Institutional Animal Care and Use Committees of the University of Colorado and University of Chicago. An ex vivo model consisting of viable bovine myocardium, a circulating saline bath at 37 degrees Celsius, a submersible load cell, and a deflectable sheath was assembled. The circulating bath utilized a perfusion pump designed for cardiac bypass and circulated fluid in a saline bath at a rate of 5 L per minute. A load cell was submersed in the bath and contained a section of viable bovine ventricular myocardium excised within 1 hour of experimentation. This load cell measured force applied to the overlying myocardial tissue and was used to standardize application of energy. This ex vivo model has been validated and described in further detail elsewhere [Olson M D, et al., *J Interv Card Electrophysiol* 0.38:123-129].

Figure 24:
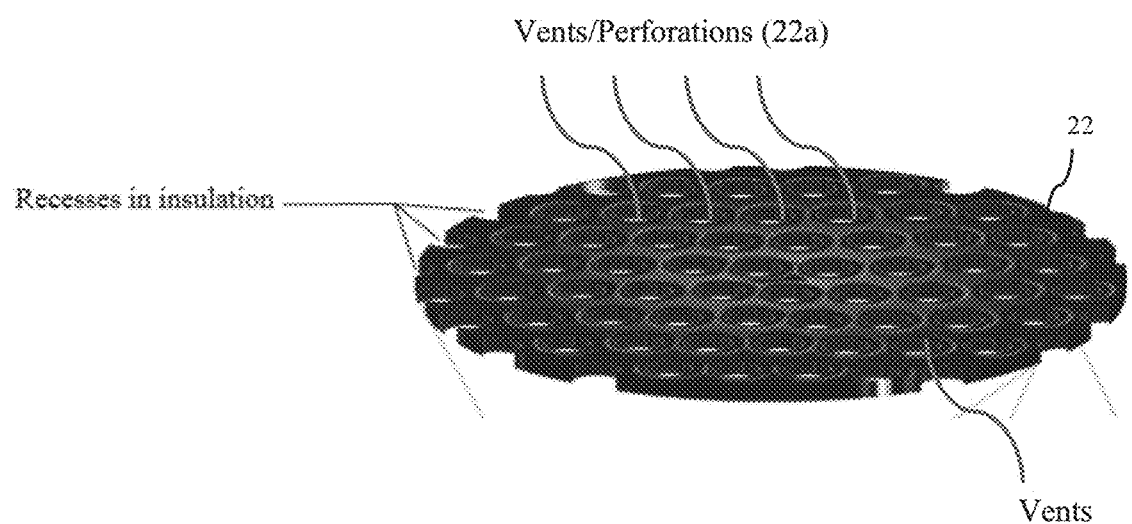
FIG. 24 is an illustration of the vents in the insulation of a radiofrequency venting catheter.

Catheter Modification with Electrical Insulation Using Thermally Conductive Materials A non-irrigated 4 mm RF catheter, non-irrigated 8 mm RF catheter, and an open-irrigated RF ablation catheter (Biosense-Webster, Diamond Bar, Calif.) were partially insulated by coating half their surfaces with a thin layer of thermally conductive material, including either a layer of vinyl, silicone, vinyl-silicone, polyurethane, or a composite of aluminum oxide/boron nitride (AOBN) (See e.g. FIGS. 12, 15-20 and 23). The coatings were created with an epoxy allowed to dry, leaving a thin (<0.1 mm) layer covering half of the metallic tip. For the externally irrigated catheter, the existing tip fenestrations were preserved to allow for active cooling with saline irrigant on all sides of the catheter. These PIFA catheters or their corresponding non-insulated catheters (Biosense-Webster, Diamond Bar, Calif.) were positioned with 10 grams of force in a parallel position using a deflectable sheath (Agilis, St. Jude Medical). The most effective insulation coating, AOBN, a very effective insulation coating, was further modified by adding vents into the coating to allow for thermal release/venting (FIGS. 23 and 24). Ablation with this vented AOBN was compared to standard AOBN coating, and temperatures were recorded.

Delivery of Radiofrequency Energy Applied to Myocardium

Using varying powers (20, 30, and 40 Watts) under power control mode, a series of ablation lesions with each catheter was created on the recently excised bovine myocardium, with the insulated or non-insulated side parallel to the myocardium. A separate set of lesions was created using temperature control mode for maximum power (50 Watts for 4 mm and irrigated tip and 70 W for 8 mm), with tip temperature limits set at ≤55° C. (4 mm), ≤60° C. (8 mm) and ≤45° C. (irrigated tip), for 60-second ablations. The number of lesions applied per ventricular section depended upon the available endocardial surface. No lesions were placed over or in immediate proximity of papillary muscles (5 mm) or within immediate proximity of other lesions. Furthermore, no lesions were placed within 1 cm of section edge.

In Vivo Epicardial Ablation and Assessment of Pericardial Injury

Three Yorkshire pigs were anesthetized and intravenous lidocaine (50-100 mg) was used intraoperatively for prophylaxis of ventricular arrhythmias. Epicardial access was obtained under fluoroscopy using a 17-gauge Pajunk needle (Pajunk Medical Systems, Norcross, Ga.) and a 9 French sheath was placed in the epicardium. An electroanatomic map of the entire epicardium was created using the CARTO3 mapping system (Biosense-Webster, Diamond Bar, Calif.). Via the 9 French sheath, a PIFA irrigated tip catheter and a standard irrigated tip catheter were used to deliver PIFA and standard irrigated "control" ablation lesions on the epicardium in each pig. Ablations were delivered at 50 W for 30 seconds with the same amount of force as measured by SmartTouch technology on the RF catheters (Biosense-Webster, Diamond Bar, Calif.); ablation lesions were tagged by the electroanatomic mapping system. Ablations with both PIFA and standard catheters were performed in the same epicardial region. Saline irrigant was suctioned from the epicardium after each ablation. Following ablation, animals were sacrificed and the hearts and their pericardium were immediately explanted and fixed in formalin. Gross pathology was performed; pericardial tissue were assessed for injury, and epicardial ablation lesions were analyzed.

In Vivo Ablation of AV Node and Phrenic Nerve

Yorkshire pigs (n=12) were anesthetized and intravenous lidocaine (50-100 mg) or amiodarone (150 mg IV bolus followed by a 1 mg/min infusion) was used intraoperatively for prophylaxis of ventricular arrhythmias. Epicardial access was obtained under fluoroscopy using a 17-gauge Pajunk needle (Pajunk Medical Systems, Norcross, Ga.) and a 9 French sheath was placed in the epicardium. An electroanatomic map of the superior vena cava (SVC), right atrium (RA), and epicardium was created using the CARTO3 mapping system (Biosense-Webster, Diamond Bar, Calif.).

A decapolar catheter was used to pace and capture the right and left phrenic nerves, either in the endocardium or epicardium. A force-sensing PIFA irrigated tip catheter and a standard force-sensing irrigated tip catheter were used to deliver alternating PIFA and standard irrigated "control" ablation lesions directly below the site of phrenic nerve capture. After each ablation, pacing and capture of the phrenic nerve was moved inferiorly. Loss of phrenic nerve capture, time to loss of phrenic nerve capture, and time to phrenic nerve recovery (as established by return of phrenic nerve capture) were recorded and compared for PIFA and control. During PIFA ablation, the insulated aspect of the catheter tip was superiorly oriented toward the phrenic nerve. Ablations were delivered at 50 W for 30 seconds with the same amount of force as measured by SmartTouch technology on the RF catheters (Biosense-Webster, Diamond Bar, Calif.); ablation lesions were tagged by the electroanatomic mapping system. Saline irrigant was suctioned from the epicardium after each ablation.

The Bundle of His was mapped on the septal tricuspid annulus. Once the His region was annotated, either a standard irrigated catheter or a PIFA catheter was placed directly below the His and ablation was performed. AV block, time to AV block, and recovery of conduction after immediate cessation of ablation, if any, were recorded. During PIFA ablation, the insulated aspect of the catheter tip was superiorly oriented toward the His. Ablations were delivered at 50 W for 30 seconds with the same amount of force as measured by SmartTouch technology on the RF catheters (Biosense-Webster, Diamond Bar, Calif.); ablation lesions were tagged by the electroanatomic mapping system.

Ablation Lesion Volume Measurements

Lesion volumes were acquired by analyzing tissue sections with a digital micrometer.

Single lesion volumes were calculated using the equation for an ellipsoid. For each lesion, maximum depth (A), maximum width (W), and lesion surface diameter (D) were measured.

Volume of an Ellipsoid Ablation Lesion:

$$LesionVolume = \left[1.33\pi(D)\left(\frac{W}{2}\right)\left(\frac{L}{2}\right)\right]/2$$

Where D=maximum depth, W=maximum width, and L=Lesion surface diameter

Ablation Lesion Volume Measurements

Lesion volumes were acquired by analyzing tissue sections with a digital micrometer. Single lesion volumes were calculated using the equation for an oblate ellipsoid. For each lesion, maximum depth (A), maximum diameter (B), depth at maximum diameter (C), and lesion surface diameter (D) were measured.

$$LesionVolume = \left[0.75\pi\left(\frac{B}{2}\right)^2(A-C)\right] - \left[0.25\pi\left(\frac{D}{2}\right)^2(A-2C)\right]$$

Equation 2: volume of oblate ellipsoid

Where A=maximum depth, B=maximum diameter, C=depth at maximum diameter and D=lesion surface diameter.

Tissue Temperature Analysis

Figure 2:
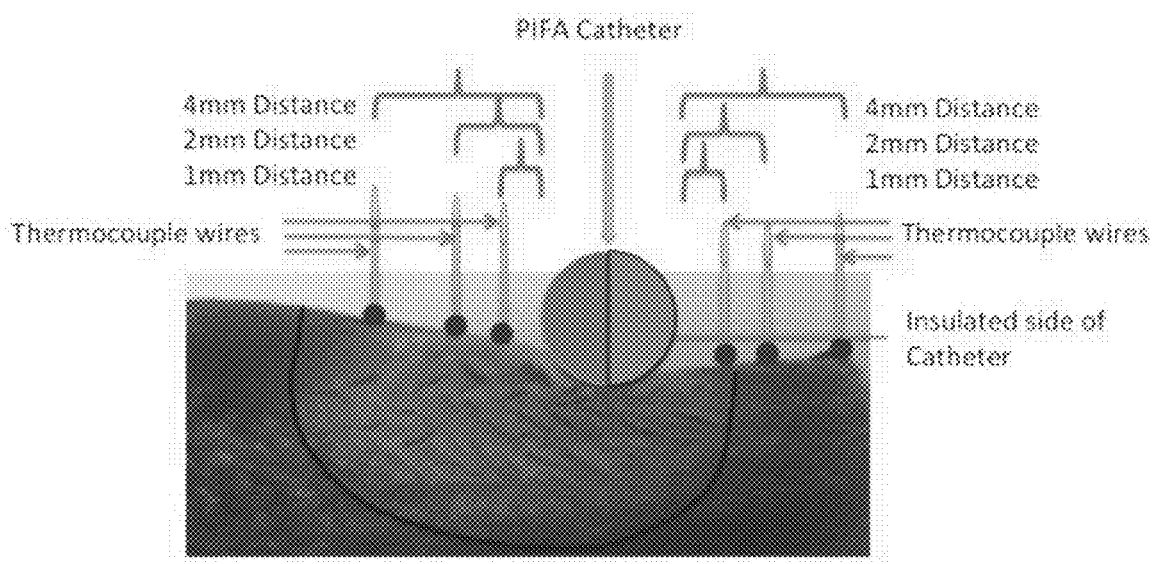
FIG. 2 is an image illustrating PIFA catheter and thermocouple positions for surface temperature measurements. Thermocouple wire tips are placed on the myocardial surface on either side of the PIFA catheter at 1, 2, and 4 mm distance from the catheter.

T-type thermocouple wires were inserted horizontally into myocardium at 3 mm and 5 mm depths and beneath the ablation surface during ablations with the standard catheter or non-insulated aspect of the PIFA catheter parallel to the myocardium (FIGS. 1 and 2). Furthermore, T-type thermocouple wires were placed horizontally into myocardium at 1 mm, 2 mm, and 4 mm distances from each side of the ablation catheter, with the ablation catheter oriented as shown in FIG. 2 in relationship to the myocardium. Thermocouple analogue inputs were converted to digital signals using LabView software (version 7.0). Temperatures were recorded in a continuous fashion throughout the 60 seconds of RF application at a rate of 5 Hertz. Peak tissue temperature was defined as the maximum temperature reading during RF application. Initial temperature rise rate was defined as the amount of temperature rise in the first 30 seconds and area under curve (AUC) corresponded to total temperature change over total RF time (60 seconds). RF applications that generated steam pops were excluded from temperature curve analysis.

Statistical Analysis

SPSS software was used to perform all calculations. The Analysis of Variance (ANOVA) test was used to compare continuous variables and the Chi-square test was used for dichotomous comparisons in lesion characteristics from PIFA catheter-ablated myocardium vs. lesions ablated by corresponding non-insulated catheters.

Example 2—Effect of Partial Insulation on Ablation Lesion Geometry and Volume Using Low and High Power Radiofrequency Energy At 20 W, ablation lesions (n=12) created by the 4 mm PIFA catheter were significantly larger, 101 mm$^3$ vs. 35 mm$^3$ ($p<0.001$; n=18). This effect was similar for the 8 mm PIFA catheter, compared to a standard 8 mm catheter, at varying powers from 30 W to 60 W (the standard 8 mm catheter created negligible lesions at 20 W, and these were unable to be used for comparisons to the 8 mm PIFA lesions at 20 W). The same phenomenon was observed for the open irrigated catheter at 20 W, with the PIFA irrigated catheter creating volumes of 75.4 mm$^3$, compared to 22.1 mm$^3$ ($p<0.001$) for the standard open irrigated catheter. Ablation lesions could not be created on tissue exposed to the insulated side of each PIFA catheter. Tables 1 and 2 show the differences in ablation lesion shape and size, depending on the catheter used. The tip temperatures for all ablation lesions created with all catheters tested were <55° C. (4 mm and 8 mm) and <45° C. (irrigated tip) at the fixed powers tested.

TABLE 1

Myocardial Ablation Lesion Characteristics after Radiofrequency Energy Applied at 20 Watts for 60 Seconds

|  | Standard 4 mm Catheter (N =18) | 4 mm PIFA Catheter (N =12) | P value (4 mm vs. PIFA 4 mm) | Standard open irrigated (N =18) | PIFA open irrigated (N =14) | P value (Open irrigated vs. PIFA) |
|---|---|---|---|---|---|---|
| Maximum Depth (mm) | 2.3 ± 0.6 | 4.8 ± 0.3 | <0.001 | 1.8 ± 0.4 | 4.6 ± 0.5 | <0.001 |
| Maximum Width (mm) | 4.8 ± 0.9 | 5.6 ± 0.6 | =0.004 | 3.7 ± 0.4 | 4.8 ± 0.5 | <0.001 |
| Surface Diameter (mm) | 5.9 ± 0.8 | 7.2 ± 0.6 | <0.001 | 6.2 ± 0.4 | 6.6 ± 0.6 | <0.05 |
| Volume (mm$^3$) | 35.0 ± 12.5 | 101.0 ± 17.4 | <0.001 | 22.1 ± 7.0 | 75.4 ± 17.2 | <0.001 |
| Peak Temp at 3 mm (° C.) | 60.0 ± 7.4 | 75.3 ± 8.7 | <0.001 | 55.9 ± 4.5 | 71.6 ± 9.3 | <0.001 |
| Peak Temp at 5 mm (° C.) | 47.4 ± 4.0 | 53.6 ± 4.7 | <0.001 | 51.9 ± 3.8 | 61.8 ± 8.9 | <0.001 |

TABLE 2

Myocardial Ablation Lesion Characteristics after Radiofrequency Energy with 8 mm Ablation Catheter, Applied at 30 W and 60 W for 60 Seconds

|  | 30 W Standard 8 mm Catheter (N = 14) | 30 W PIFA 8 mm Catheter (N=15) | 30 W P value (8 mm vs. PIFA 8 mm) | 60 W Standard 8 mm Catheter (N = 16) | 60 W PIFA 8 mm Catheter (N = 17) | 60 W P value (8 mm vs. PIFA 8 mm) |
|---|---|---|---|---|---|---|
| Maximum Depth (mm) | 2.1 ± 0.4 | 3.9 ± 0.7 | <0.001 | 4.1 ± 0.6 | 5.6 ± 0.5 | <0.001 |
| Maximum Width (mm) | 4.2 ± 0.3 | 4.2 ± 0.5 | =0.989 | 4.4 ± 0.4 | 5.4 ± 0.4 | <0.001 |

TABLE 2-continued

Myocardial Ablation Lesion Characteristics after Radiofrequency Energy with 8 mm Ablation Catheter, Applied at 30 W and 60 W for 60 Seconds

|  | 30 W Standard 8 mm Catheter (N = 14) | 30 W PIFA 8 mm Catheter (N=15) | 30 W P value (8 mm vs. PIFA 8 mm) | 60 W Standard 8 mm Catheter (N = 16) | 60 W PIFA 8 mm Catheter (N = 17) | 60 W P value (8 mm vs. PIFA 8 mm) |
|---|---|---|---|---|---|---|
| Surface Diameter (mm) | 9.0 ± 0.6 | 10.0 ± 0.9 | =0.002 | 9.4 ± 0.4 | 10.8 ± 0.8 | <0.001 |
| Volume (mm$^3$) | 40.9 ± 10.0 | 85.8 ± 18.1 | <0.001 | 90.1 ± 17.6 | 170.6 ± 26.5 | <0.001 |
| Peak Temp at 3 mm (° C.) | 53.3 ± 4.5 | 72.4 ± 12.0 | <0.001 | | | |
| Peak Temp at 5 mm (° C.) | 49.1 ± 3.5 | 60.1 ± 7.4 | <0.001 | | | |

Example 3—Effect of Partial Insulation on Tip Temperatures and Lesion Sizes with RF Energy Delivery Using Temperature Control Mode Temperature control ablation was performed for each PIFA catheter and its corresponding catheter (Table 3). For the 4 mm catheters, maximum power was set to 50 W and catheter tip temperature limit set to 55° C. Peak catheter tip temperatures were statistically different between PIFA and standard 4 mm catheters, 53±3° C. vs. 46±2° C. respectively (p<0.001); however, the PIFA 4 mm catheter was not significantly limited by these peak temperatures, as it was able to achieve a maximum power of 49±1 W, which was not statistically different from the 50 W achieved by the 4 mm standard catheter. Lesion sizes were larger with the 4 mm PIFA, measuring 169.7 mm$^3$, compared to 94.2 mm$^3$ for a standard catheter (p<0.001). There were no steam pops. Results were similar for the 8 mm and irrigated PIFA catheters, compared to their corresponding catheters, using temperature control mode ablation. While catheter tip temperatures were higher for the PIFA catheters (Table 3), power delivery was not limited, and maximum powers (70 W for 8 mm, 50 W for irrigated tip) were achieved and larger lesions were created.

TABLE 3

Catheter Tip Temperatures and Lesion Characteristics with Radiofrequency Energy Delivery Using Temperature Control Mode

|  | Standard 4 mm | 4 mm PIFA | P-value | Standard 8 mm | 8 mm PIFA | P-Value | Standard Irrigated | Irrigated PIFA | P-Value |
|---|---|---|---|---|---|---|---|---|---|
| N | 10 | 10 |  | 10 | 10 |  | 10 | 10 |  |
| Temp Control (° C.) | 55 | 55 |  | 60 | 60 |  | 45 | 45 |  |
| Max Power Set (W) | 50 | 50 |  | 70 | 70 |  | 50 | 50 |  |
| Max Power Achieved (W) | 50 ± 0 | 49 ± 1 | NS | 70 ± 0 | 70 ± 0 | NS | 50 ± 0 | 50 ± 0 | NS |
| Peak Tip Temp (° C.) | 46 ± 2 | 53 ± 3 | p < 0.001 | 48 ± 2 | 53 ± 2 | p < 0.001 | 41 ± 1 | 42 ± 2 | p < 0.001 |
| Max Depth (mm) | 4.2 ± 0.5 | 5.7 ± 0.4 | p < 0.001 | 4.3 ± 0.5 | 6.6 ± 0.5 | p < 0.001 | 4.7 ± 0.4 | 6.2 ± 0.3 | p < 0.001 |
| Max Width (mm) | 5.8 ± 0.5 | 6.9 ± 0.6 | p < 0.001 | 6.1 ± 0.3 | 6.7 ± 0.5 | p = 0.010 | 5.9 ± 0.5 | 6.9 ± 0.3 | p = 0.010 |
| Surface Diameter (mm) | 7.2 ± 0.7 | 8.3 ± 0.6 | p = 0.002 | 9.3 ± 0.2 | 11.7 ± 0.8 | p < 0.001 | 7.2 ± 0.5 | 7.9 ± 0.6 | p < 0.001 |
| Volume (mm$^3$) | 94.2 ± 23.3 | 169.7 ± 30.5 | p < 0.001 | 126.2 ± 12.7 | 270.6 ± 31.3 | p < 0.001 | 103.3 ± 15.8 | 176.5 ± 20.5 | p < 0.001 |

Figure 3A:
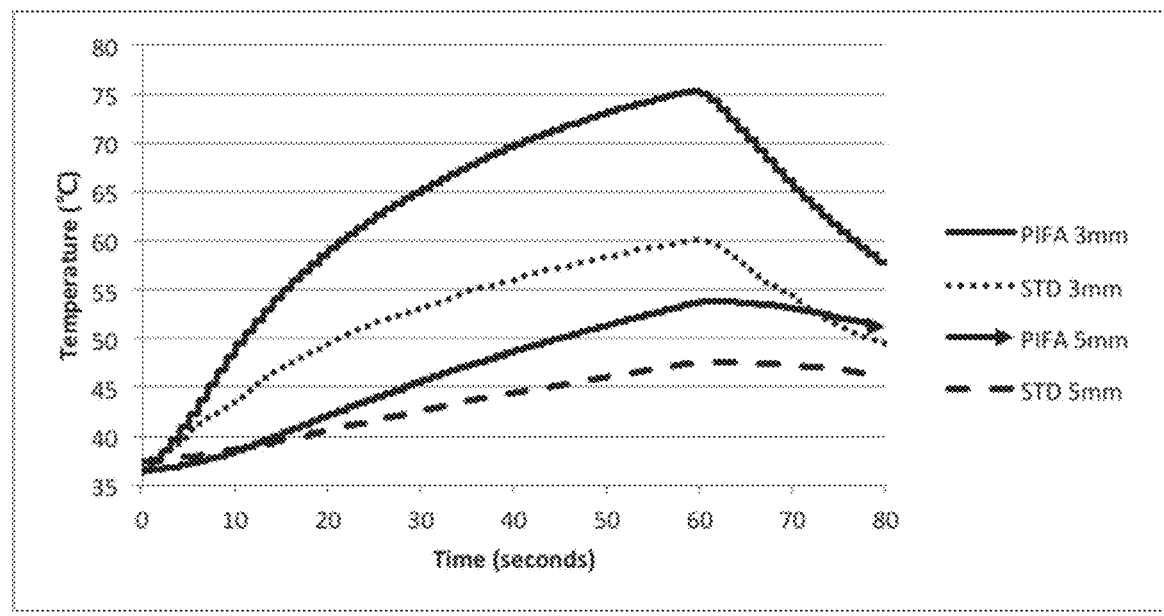
FIG. 3A is a graph illustrating the mean temperature dispersion at 3 and 5 mm depths for 20 W beneath the non-insulated side of a 4 mm PIFA catheter vs. a 4 mm standard (STD) catheter. The upper solid line is the PIFA 3 mm catheter, while the lower solid line (with arrowhead) is the PIFA 5 mm. The upper dotted line is the STD 3 mm, while the lower dashed line is the STD 5 mm.
Figure 3B:
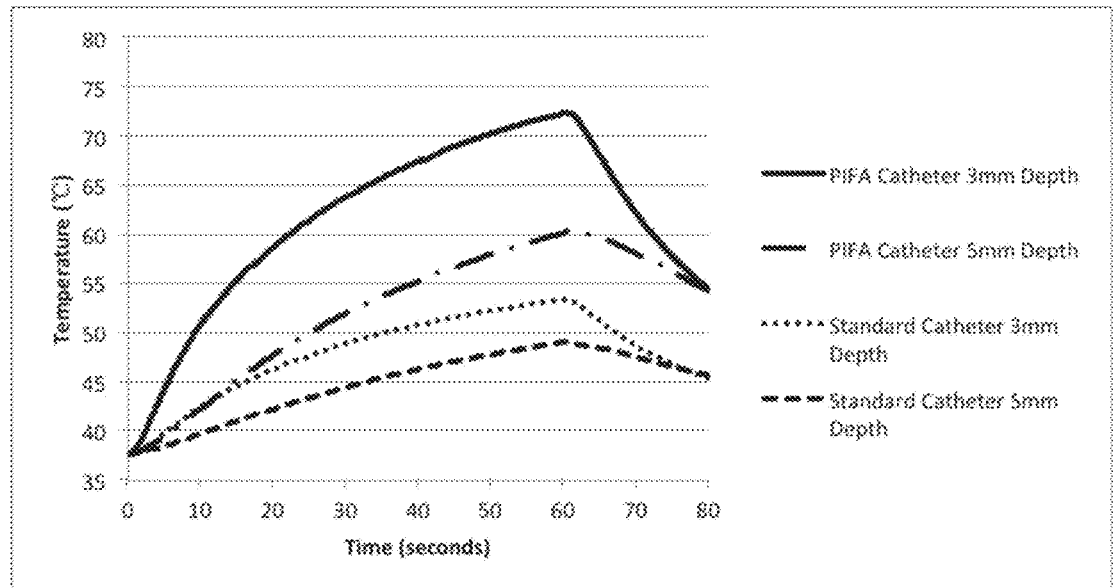
FIG. 3B is a graph illustrating the mean temperature dispersion at 3 and 5 mm depths beneath the non-insulated side of an 8 mm PIFA catheter-ablated myocardium compared to a standard 8 mm ablation catheter. The upper solid line is the PIFA at 3 mm, while the line immediately below is the PIFA catheter at 5 mm. The dotted line is the STD at 3 mm, while the lower dashed line is the STD at 5 mm.
Figure 3C:
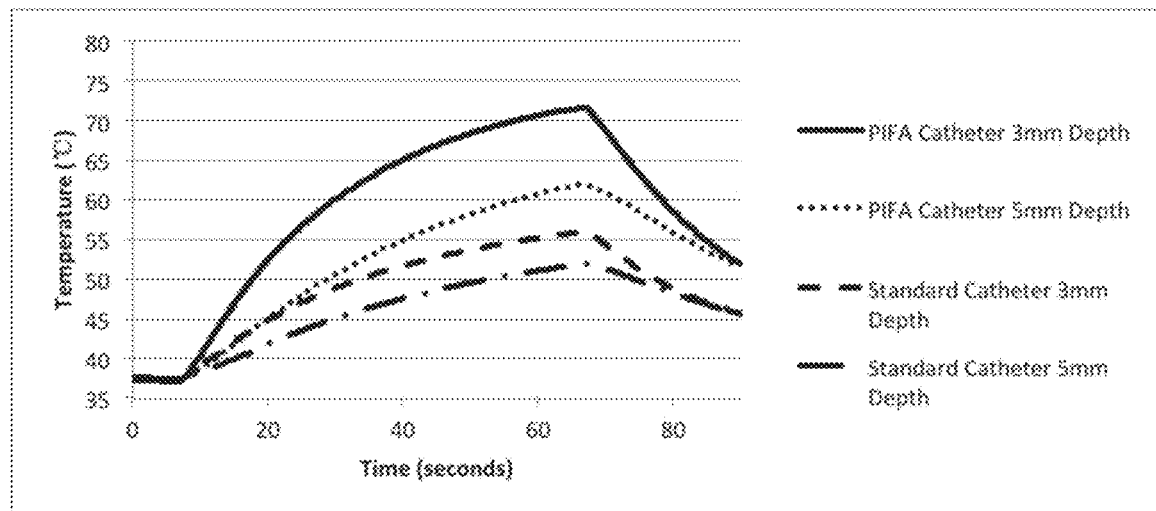
FIG. 3C is a graph illustrating the mean temperature dispersion at 3 and 5 mm depths beneath the non-insulated side of an open irrigated PIFA catheter-ablated myocardium compared to a standard open irrigated ablation catheter. The upper solid line is the PIFA at 3 mm, while the dotted line is the PIFA at 5 mm. The upper dotted line is the STD at 3 mm, while the lower dashed line is the STD at 5 mm.

Example 4—Effect of Partial Insulation on Myocardial Tissue Temperature Dispersion During a 60 second ablation at 20 Watts (power control mode), the mean temperatures recorded at 3 mm and 5 mm depths beneath the 4 mm ablation catheter tip were significantly higher with ablation using the PIFA catheter, compared to a standard 4 mm catheter (FIG. 3A). This effect was seen also for the 8 mm PIFA (FIG. 3B) and PIFA open irrigated catheters (FIG. 3C), in comparison to their corresponding catheters (peak temperatures at 3 mm and 5 mm depths provided in Tables 1 and 2).

Figure 4A:
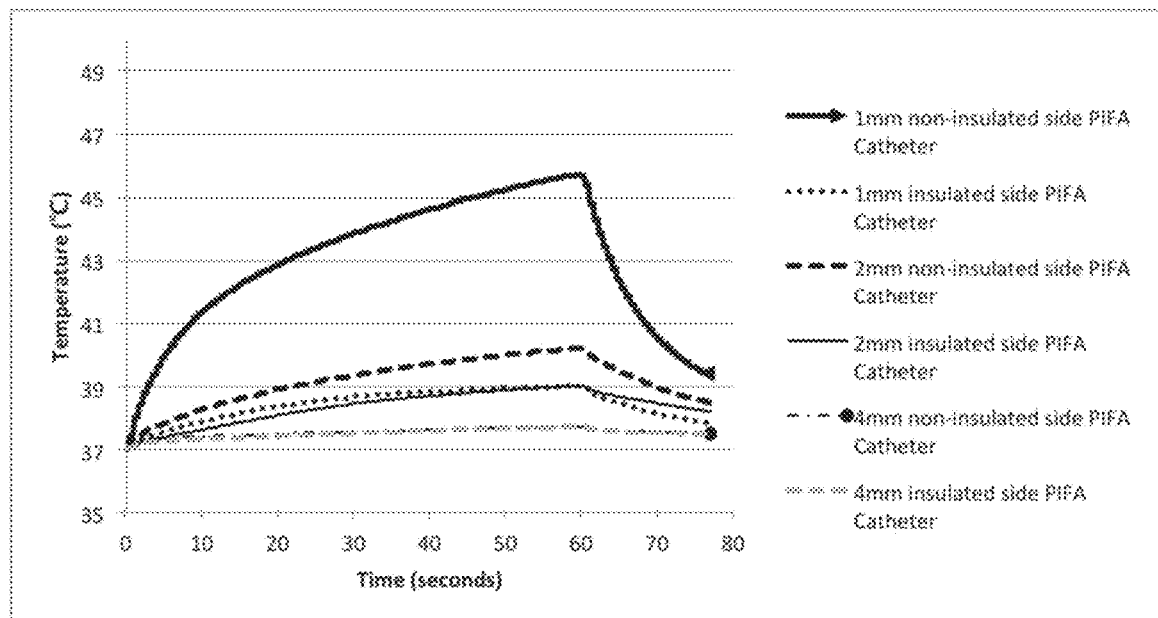
FIG. 4A is a graph illustrating the mean surface temperature dispersion at 1 mm, 2 mm, and 4 mm distances from each side (insulated, non-insulated) of a 4 mm PIFA catheter.

In addition, when measuring surface temperatures at distances of 1 mm, 2 mm, and 4 mm from each side of the PIFA ablation catheter, there were differences in mean tissue temperatures on each side of the 4 mm PIFA catheter (FIG. 4A-C). Ablation on the insulated side of the PIFA catheter resulted in a lower temperatures at 1 mm, 2 mm, and 4 mm distances, compared to both surfaces of a standard 4 mm catheter, as well as the non-insulated side of the PIFA catheter. These findings were also similar for the 8 mm and irrigated PIFA. Table 4 provides the differentials between peak temperatures at 1 mm, 2 mm, and 4 mm distance from each side of the PIFA catheters, compared to their respective standard catheter. Shallow surface temperatures on the insulated side of the PIFA catheter were similarly low compared to those of a standard open irrigated catheter due to the unchanged open irrigation cooling effect (Table 4).

TABLE 4

Differential Surface Temperature Dispersion Between Insulated and Non-insulated Sides of PIFA Catheters, Compared to Standard Catheters

|  | 4 mm PIFA | 4 mm Standard | P-value | 8 mm PIFA | 8 mm Standard | P-Value | Irrigated PIFA | Irrigated Standard | P-Value |
|---|---|---|---|---|---|---|---|---|---|
| N | 16 | 25 |  | 16 | 16 |  | 16 | 16 |  |
| Peak Differential Surface Temps 1 mm (° C.) | 6.7 ± 1.4 | 0.1 ± 0.9 | p < 0.001 | 3.7 ± 2.8 | 0.2 ± 2.1 | p < 0.001 | 2.5 ± 2.9 | 0.2 ± 2.9 | p = 0.031 |
| Peak Differential Surface Temps 2 mm (° C.) | 1.2 ± 0.9 | 0.1 ± 0.8 | p < 0.001 | 2.2 ± 0.7 | 0.1 ± 0.7 | p < 0.001 | 1.6 ± 1.5 | 1.3 ± 1.8 | p = 0.612 |
| Peak Differential Surface Temps 4 mm (° C.) | 0.03 ± 0.3 | 0.05 ± 0.5 | p = 0.455 | 0.5 ± 0.3 | 0.02 ± 0.4 | p = 0.002 | 0.9 ± 1.1 | 0.8 ± 1.4 | p = 0.890 |

Figure 5A:
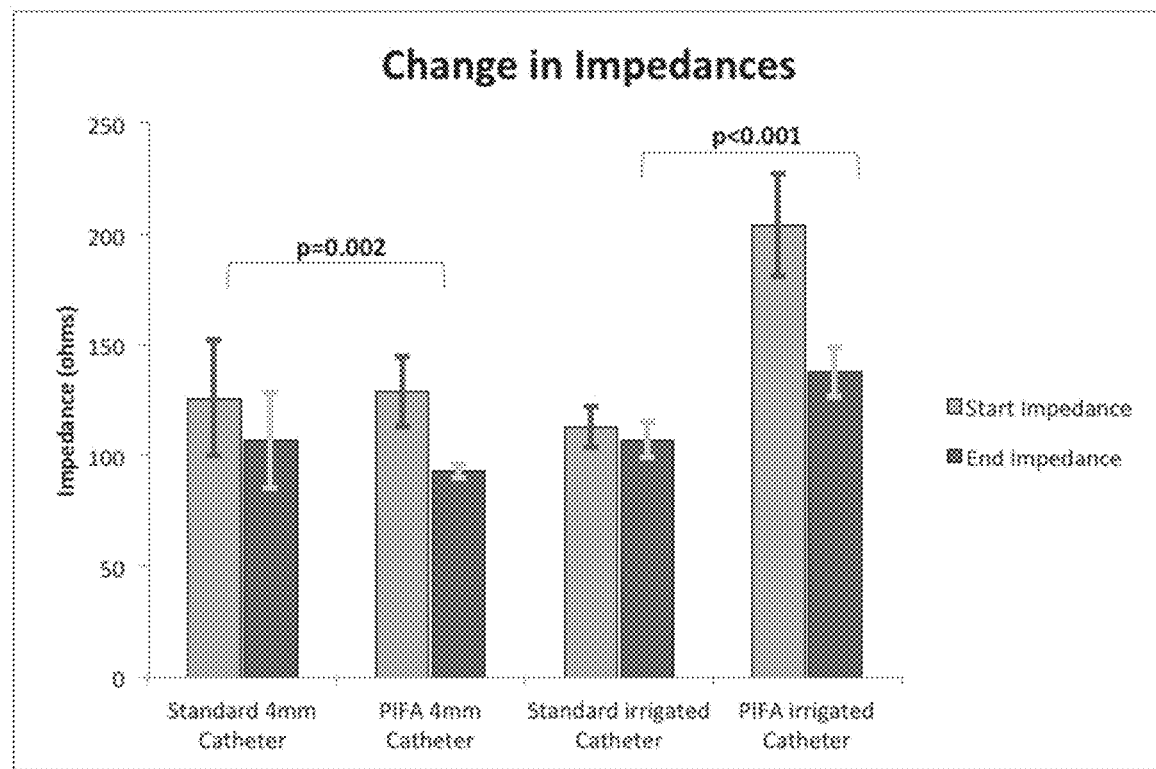
FIG. 5A is a graph illustrating the change in impedance (mean starting and ending impedance) measurements in myocardial tissue before and after ablation at 20 Watts using a 4 mm PIFA catheter and an open irrigated PIFA catheter. Compared to their corresponding standard catheters, the 4 mm PIFA and open irrigated PIFA catheter-ablated myocardial tissues had higher starting and ending impedances with a larger impedance reductions observed with ablation. This was similar for the 8 mm PIFA catheter results at both 30 Watts and 60 Watts (FIG. 5B).
Figure 5B:
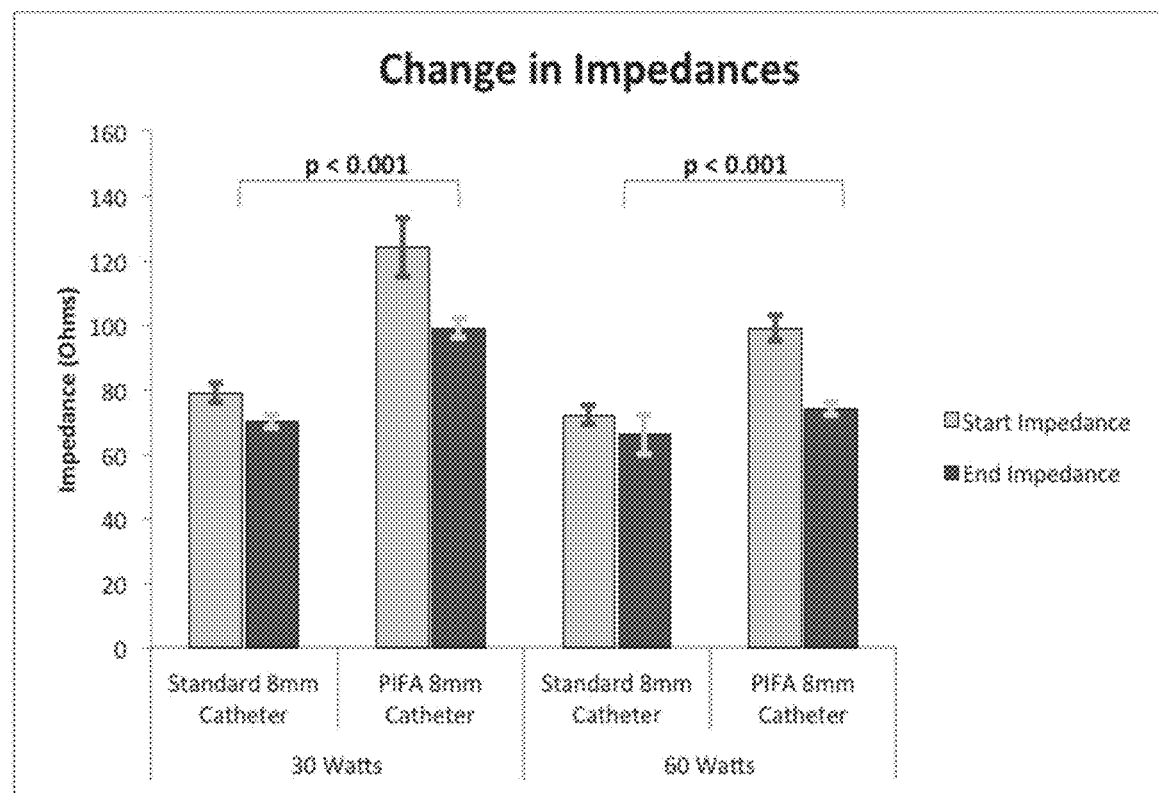
FIG. 5B is a graph illustrating the change in impedance (mean starting and ending impedance) measurements in myocardial tissue for the 8 mm PIFA catheter results at both 30 Watts and 60 Watts.
Figure 7A:
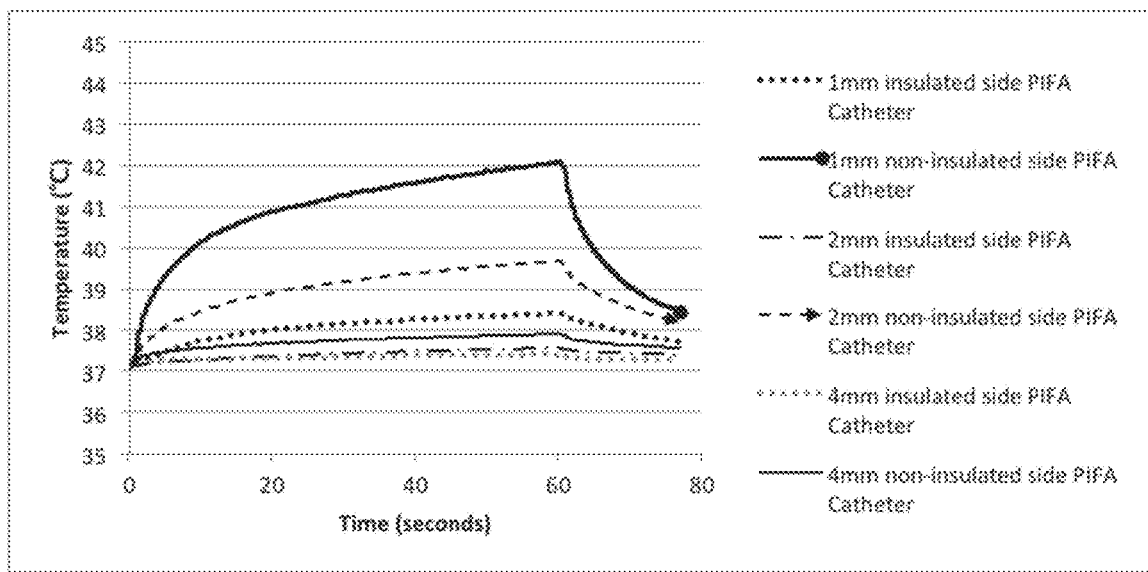
FIG. 7A is a graph illustrating the mean surface temperature dispersion at 1 mm, 2 mm, and 4 mm distances from each side (insulated, non-insulated) of an open irrigated PIFA catheter.
Figure 8A:
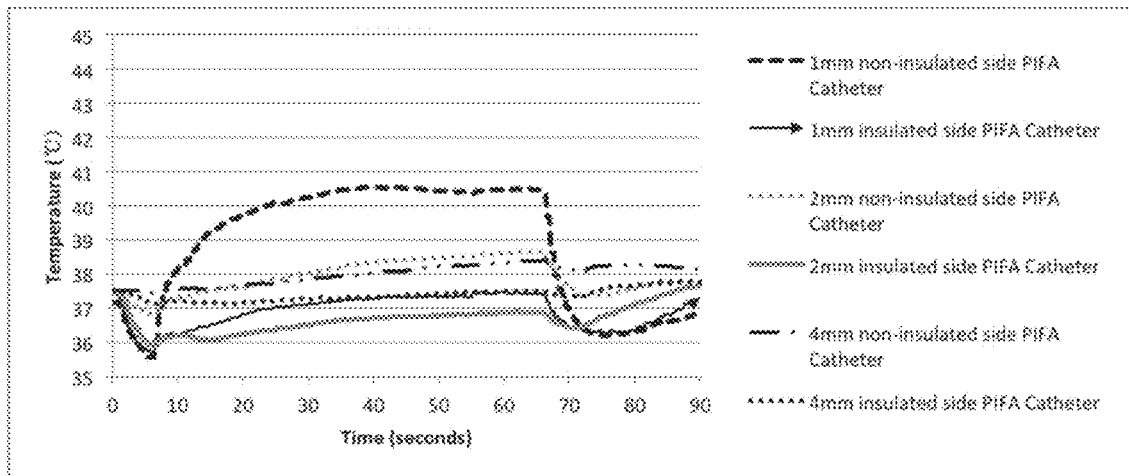
FIG. 8A is a graph illustrating the mean surface temperature dispersion at 1 mm, 2 mm, and 4 mm distances from each side (insulated, non-insulated) of a 8 mm PIFA catheter.
Figure 9:
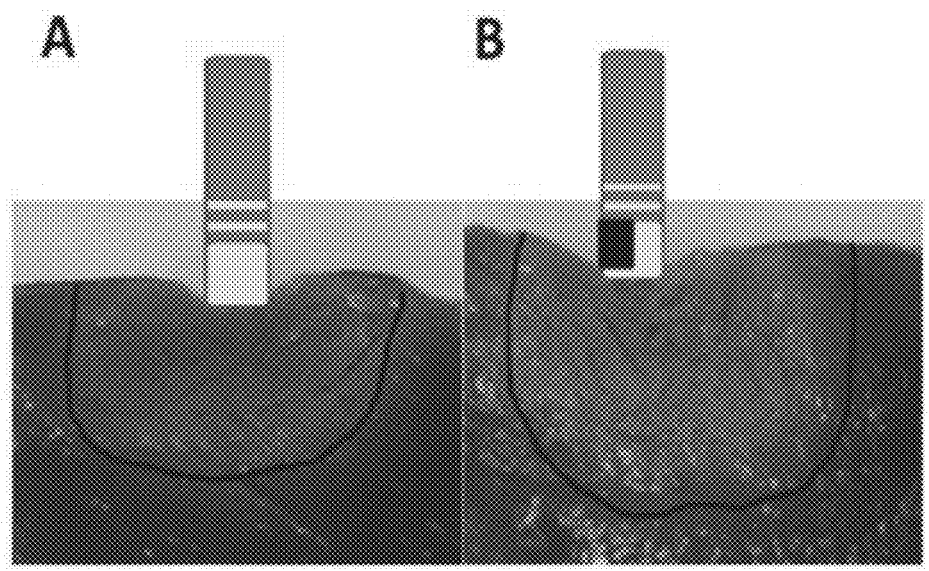
FIG. 9 is a pair of photographs illustrating the ablation lesions at 40 W for a normal catheter (A) and an insulated catheter (B).
Figure 10:
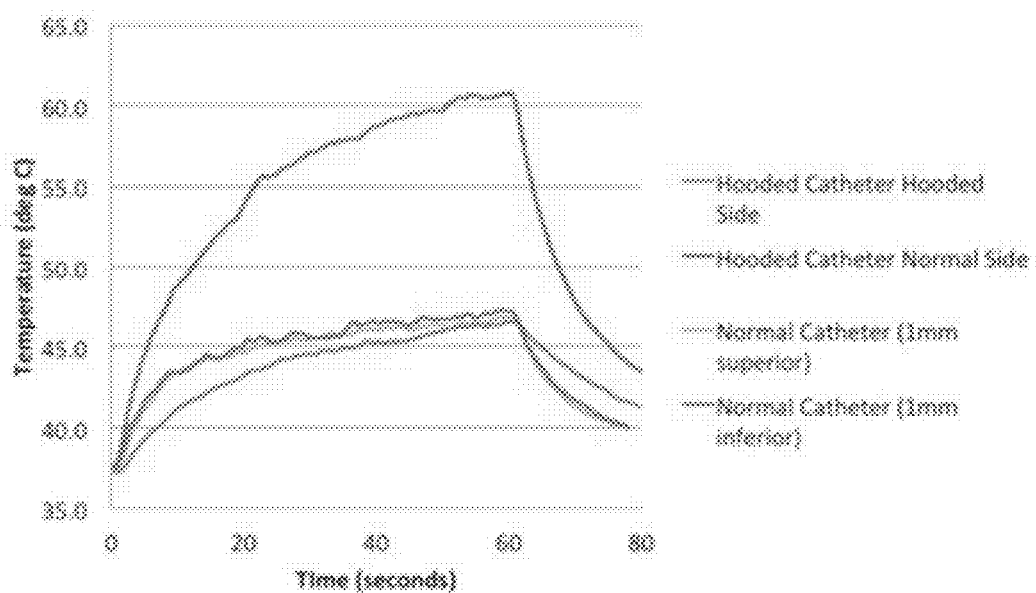
FIG. 10 is a graph illustrating the temperatures for the PIFA "hooded" catheter compared to a standard "normal" catheter.
Figure 11:
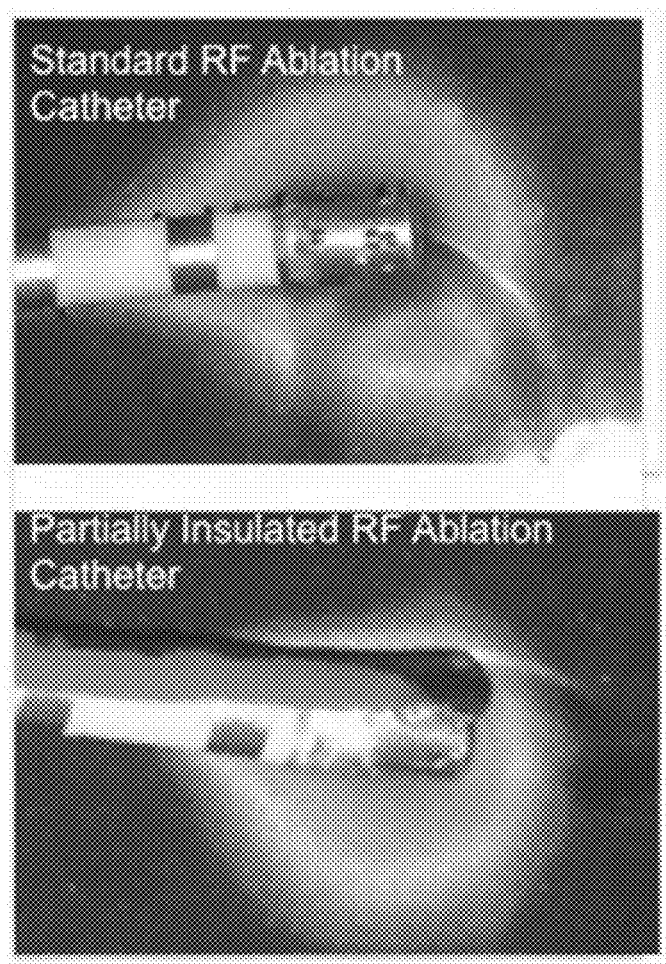
FIG. 11 is a pair of images illustrating RF heating from a "normal" catheter (above) and an insulated catheter (below) wherein the insulated catheter has a layer of insulation on the upper aspect of the catheter tip.

Example 5—Effect of Partial Insulation on Measured Electrical Impedance at the Tip-Tissue Interface FIG. 5A displays the mean starting and ending impedance measurements before and after ablation using a 4 mm PIFA catheter and open irrigated catheter. Compared to the standard ablation catheters, PIFA catheter-ablated myocardial tissues had higher starting and ending impedance with larger impedance reductions observed with ablation. These effects were also observed for the 8 mm PIFA at 30 and 60 Watts, when compared to the 8 mm standard catheter (FIG. 5B).

Example 6—Effect of Partial Insulation Catheter on the Incidence of Steam-Generated Explosions ("Steam Pops")

There were no steam pops observed at 20 Watts during RF delivery for any the 3 PIFA catheters or their corresponding standard catheters. At 30 W, ablation using the 4 mm PIFA catheter resulted in a large percentage (75%, or 6 of 8 lesions) of steam pops. The incidence of steam pops was mitigated by using irrigated tip catheters as well as by using the larger surface area of the 8 mm catheter. At 30 W, ablation using the PIFA open irrigated catheter did result in steam pops but at a lower rate (28.5%, or 4/14); no steam pops were observed with the 8 mm PIFA catheter at 30 W or 60 W. There were no steam pops at 30 W for the standard catheters.

The steam pop rates were higher for PIFA catheters with a silicone-vinyl insulation, which has decreased thermal conductivity along with its electrical insulation. Hence, in addition to using a larger surface area and open irrigation to decrease the risks of steam pops, we also repeated the studies using an improved composite insulation with more thermal conductivity while maintaining electrical insulation. Using this composite of aluminum oxide and boron nitride, we did not have steam pops at 30 or 50 W for the PIFA 4 mm catheter. Furthermore, ablation at 30 W with an open irrigated PIFA using this composite insulation also did not result in any steam pops.

Example 7—Protection of Adjacent Structures During RF Ablation with an Externally Irrigated PIFA Catheter in an In Vivo Porcine Model As a proof-of-concept experiment, three pigs underwent ablation using PIFA catheters. One of the potential side effects of epicardial ablation includes significant pericarditis, resulting from likely collateral ablation of the parietal pericardium. After epicardial access in three pigs, open irrigated PIFA ablation was performed. In the same 3 pigs, standard open irrigated control lesions were also performed in similar regions. Although the number of lesions was few (Table 5), there was a statistically significant difference in lesion sizes, 255.8 mm$^3$ for PIFA lesions vs. 56.9 mm$^3$ for control lesions, p=0.042. Furthermore, the pericardium adjacent to two control lesions demonstrated significant injury, compared to none for the PIFA lesions (FIG. 6).

TABLE 5

In vivo Epicardial Ablation of Porcine Model using PIFA Open Irrigation Catheter

|  | Standard Open Irrigated Catheter (N = 7) | PIFA Open Irrigated Catheter (N = 6) | P value (4 mm vs. PIFA 4 mm) |
|---|---|---|---|
| Maximum Depth (mm) | 3.7 ± 0.5 | 6.3 ± 2.5 | p = 0.021 |
| Maximum Diameter (mm) | 6.7 ± 1.3 | 10.5 ± 2.6 | p = 0.007 |

TABLE 5-continued

In vivo Epicardial Ablation of Porcine Model using PIFA Open Irrigation Catheter

| | Standard Open Irrigated Catheter (N = 7) | PIFA Open Irrigated Catheter (N = 6) | P value (4 mm vs. PIFA 4 mm) |
|---|---|---|---|
| Surface Diameter (mm) | 6.1 ± 1 | 9.1 ± 1.9 | p = 0.005 |
| Volume (mm$^3$) | 56.9 ± 24.2 | 255.8 ± 228.3 | p = 0.042 |

The partially insulated ablation catheters have been shown herein to exhibit significantly altered radiofrequency ablation properties. Specifically, in the examples, ablation of myocardial tissue with partially insulated catheters resulted in an increase in ablation lesion size beneath the non-insulated PIFA surfaces, while myocardial tissue on the insulated sides were protected and had only trivial evidence of ablation. The larger lesions created by the non-insulated sides of the PIFA catheters were associated with a larger reduction in electrical impedance and improved thermal conductivity below the non-insulated surfaces. Lesion sizes were insignificant and temperatures were lower for the insulated surfaces of PIFA catheters.

By insulating a portion of a standard ablation catheter, the effective current density on the remaining non-insulated metallic tip used for RF energy delivery is greatly increased, therefore leading to larger and, depending on catheter orientation, asymmetric lesions. Furthermore, in addition to having a smaller RF conductive surface area, there may also be an enhanced "edge effect" with partial insulation, due to the resultant semi-circular exposed metal of the modified ablation catheter. Besides the increased RF current density compared to standard non-insulated catheters, the non-irrigated PIFA catheters also demonstrated significant comparative reduction in RF heating of tissue along the insulated side. However, this reduction in heating on the insulated side was not significant for the open irrigated PIFA catheter. This may be due to the fact that the insulation decreased the saline flow through the catheter's bores on the insulated side, thereby preventing the full effects of saline irrigation on decreasing temperatures. Hence, although the insulation decreased temperatures, its effects were similar to, but not necessarily different than, open irrigation that is actively cooling that side of the catheter. An insulated open irrigation catheter that preserves the same degree of active cooling on the insulated side would exhibit a further decrease in tissue temperatures.

In 1995, Panescu and colleagues developed an altered tip geometry. Their device had an hour-glass shaped catheter ablation tip resulting in an increased regional current density. This was a forerunner of the 8 mm "peanut" ablation catheter. In addition to differences in the shape of an ablation catheter tip, the material used for RF conduction has also been explored. Recent investigations show increased RF heating with less electrode heating using gold ablation tips compared to standard platinum-iridium catheter tips. However, selective insulation of an ablation catheter tip has never been explored or suggested in the prior investigations seeking to improve tip performance.

Catheter ablation of cardiac tissue with radiofrequency (RF) energy is routinely performed for the treatment of a variety of arrhythmias. All radiofrequency ablation catheters are radially symmetric at the catheter tip cylinder, thus allowing for circumferential RF. However, there is an unmet need in catheter design that allows for a more tailored approach during RF ablation in which circumferential ablation is not desired. There are many circumstances where RF energy restricted to a single side of the catheter may prevent complications due to unintended collateral injury to vital structures adjacent to the targeted cardiac tissue. This situation is most commonly observed during RF application near the AV node, in the epicardium, and near the phrenic nerve. Furthermore, a circumferential catheter tip may lead to unintended loss of RF to surrounding blood flow, thus decreasing the efficacy of ablation. An insulated catheter, where RF energy is concentrated to a single side, will allow for a more effective ablation at lower powers, potentially improving safety. It will also permit RF delivery deeper into tissues and is therefore useful for difficult arrhythmias arising from deep structures such as the septum, papillary muscle, and cavo-tricuspid isthmus.

An insulated catheter has been designed and engineered, using a silicone-vinyl coating on half the surface of a catheter tip to direct RF energy preferentially and asymmetrically to the non-insulated side of the catheter tip. Ablation studies with these PIFA catheters have met two principal objectives for clinical applicability. First, it is shown herein that the insulated sides of the PIFA catheters have decreased temperature changes and minimal tissue injury when RF ablation is delivered. Secondly, it is shown that the non-insulated sides of these catheters deliver a greater degree of tissue heating with less power, which results in larger ablation lesions.

Ablation lesion dimension variations caused by external variables, such as circulation rate, passive catheter cooling, and catheter contact, were controlled by standardizing these variables upon repetitive energy delivery. Even after controlling for these variables, some variation remained in ablation lesion sizes noted with redundant energy delivery at different sites on the same section of excised myocardium, indicating uncontrolled confounding. This most likely represents local changes in ischemic myocardial tissue due to lack of perfusion, subtle changes in the angulation of the ablation catheter, and the immeasurable effect of passive cooling based on proximity to the circulating pump intake or output cannula. To reduce the impact of variable lesion size, energy delivery under similar conditions for each RF application was repeated and the mean ablation lesion size was applied when comparing the effects of partially insulated catheters. In addition, the variable conditions that may exist would be non-differential among the individual experiments.

Partially insulated ablation catheters resulted in increased lesion sizes from applied radiofrequency energy on the non-insulated surfaces of the catheters in an ex vivo model, due to increased RF current density. Partial insulation of an ablation catheter significantly altered the electrical properties at the tip-tissue interface of targeted myocardial tissue and resulted in the increased degree of RF heating. In addition, tissue adjacent to the insulated surfaces of the catheters had lower injury characteristics, with smaller ablation lesion sizes and lower temperatures.

Example 8—RF Venting Catheter

FIG. 23 shows an illustration of an RF venting catheter design. The vented ablation catheter is insulated over its superior aspect, thereby focusing ablation to the lower aspect while allowing limited heat dissipation through the insulation. The vented catheter has a plurality of perforations, or vents or pores, that provide limited exposure to the metal beneath the insulation. The addition of RF venting to the catheter insulation augments catheter cooling without compromising the safety profile and the intended protective role of the thermally conductive electrical installation.

The pore size can be tailored to address specific applications or needs. For example, larger pores will increase the exposure of the metal beneath the catheter insulation to the fluid in the area surrounding the ablation site. Thus, it is envisioned that pore sizes can vary from very fine perforations that are sparsely distributed over the surface of the insulated metal to large perforations that leave the surface of the metal largely exposed. The size of the gaps in the insulation can be important. For example, the spectrum of possible coating designs include ones like a fish net (very large "holes") and ones like perforated leather (very small holes). The insulation on the tip of the catheter essentially interferes with contact between the tip and the tissue, but allows for contact with external blood/saline for controlled RF leaking or venting when utilizing a vented design such as is proposed, thus effectively diminishing the concentration of RF current at the tip-tissue interface in a controlled manner. This augments the safety of the catheter.

Example 9—Effect of Partial Insulation on Tip Temperatures and Lesion Sizes with RF Energy Delivery Using Temperature Control Mode Partial insulation of an irrigated catheter tip with silicone and AOBN exhibited improved performance, and reduced tip temperature limitations, when compared to vinyl, vinyl-silicone, and polyurethane partial insulation. Significant differences in lesion volumes and temperature-limited powers were noted for control, silicone and AOBN tips (Tables 6 and 7). In addition, steam pops were significantly higher for silicone but not AOBN. AOBN created larger lesions, compared to controls.

TABLE 6

Myocardial Ablation Lesion Characteristics After Radiofrequency Energy Applied at 30 W (n = 10) for 60 Seconds Using Different Insulated Materials

| Thermocool Catheter | Average Max Depth (mm) | Diameter Max (mm) | Max Surface Diam (mm) | Steam Pops | Volume (mm$^3$) | Impedance Drop (Ohms) | Peak temp (□) |
|---|---|---|---|---|---|---|---|
| Standard (STD) | 2.9 ± 0.5 | 7.6 ± 0.7 | 6.1 ± 0.4 | 0/10 | 67.6 ± 17.1 | 6 ± 1 | 37 ± 1 |
| Arctic Alumina (AA) | 4.3 ± 0.3 | 7.9 ± 0.9 | 6.8 ± 0.8 | 0/10 | 97.8 ± 23.7 | 25 ± 5 | 42 ± 2 |
| Silicone (Sc) | 4.6 ± 0.4 | 8.6 ± 0.7 | 6.6 ± 0.3 | 1/14 | 130.7 ± 30.4 | 32 ± 8 | 41 ± 2 |
| Vinyl | 4.1 ± 0.4 | 8.0 ± 0.8 | 6.2 ± 0.4 | 0/10 | 93.8 ± 24.8 | 19 ± 7 | 43 ± 1 |
| Cyanoacrylate (Cy) | 4.5 ± 0.4 | 8.4 ± 0.3 | 6.8 ± 0.2 | 1/14 | 115.0 ± 12.7 | 37 ± 6 | 42 ± 1 |
| Cyan w/graphite (Cy/g) | 5 ± 0.2 | 8.4 ± 0.6 | 6.4 ± 0.4 | 2/18 | 116.2 ± 18.2 | 44 ± 11 | 42 ± 2 |
| Plastic (Pl) | 5.1 ± 0.3 | 8.9 ± 0.6 | 6.7 ± 0.5 | 1/21 | 146.1 ± 20.3 | 39 ± 10 | 39 ± 2 |
| Marine Sealant (MS) | 4.6 ± 0.3 | 8.7 ± 0.9 | 6.9 ± 0.2 | 0/10 | 121.9 ± 26.8 | 26 ± 7 | 42 ± 2 |
| AA vs. STD | p < 0.001 | p = 0.414 | p = 0.031 | p = 1 | p = 0.005 | p < 0.001 | p < 0.001 |
| Sc vs. STD | p < 0.001 | p = 0.005 | p = 0.008 | p = 0.388 | p < 0.001 | p < 0.001 | p < 0.001 |
| Vinyl vs. STD | p < 0.001 | p = 0.262 | p = 0.512 | p = 1 | p = 0.014 | p < 0.001 | p < 0.001 |
| Cy vs. STD | p < 0.001 | p = 0.007 | p < 0.001 | p = 0.388 | p < 0.001 | p < 0.001 | p < 0.001 |
| Cy/g vs. STD | p < 0.001 | p = 0.014 | p = 0.215 | p = 0.274 | p < 0.001 | p < 0.001 | p < 0.001 |
| Pl vs. STD | p < 0.001 | p < 0.001 | p = 0.019 | p = 0.483 | p < 0.001 | p < 0.001 | p = 0.001 |
| MS vs. STD | p < 0.001 | p = 0.006 | p < 0.001 | p = 1 | p < 0.001 | p < 0.001 | p < 0.001 |

TABLE 7

Myocardial Ablation Lesion Characteristics After Radiofrequency Energy Applied at 50 W (n = 10) for 60 Seconds Using Different Insulated Materials

| Thermocool Catheter | Average Max Depth (mm) | Diameter Max (mm) | Max Surface Diam (mm) | Steam Pops | Volume (mm$^3$) | Impedance Drop (Ohms) | Peak temp (□) |
|---|---|---|---|---|---|---|---|
| Standard | 4.7 ± 0.4 | 8.7 ± 0.6 | 7.1 ± 0.5 | 0/10 | 126.9 ± 29.1 | 15 ± 4 | 41 ± 1 |
| Arctic Alumina | 6.1 ± 0.4 | 9.6 ± 0.6 | 7.5 ± 0.3 | 5/29 | 210.3 ± 28.7 | 30 ± 3 | 43 ± 1 |
| silicone | Pop | | | 10/10 | | | |
| Vinyl | 5.3 ± 0.3 | 9.6 ± 0.8 | 7.2 ± 0.4 | 0/10 | 173.6 ± 29.2 | 23 ± 5 | 45 ± 2 |
| Cyanoacrylate | 5.6 ± 0.4 | 10.5 ± 1.1 | 8.3 ± 0.8 | 6/16 | 223.4 ± 52.9 | 36 ± 8 | 43 ± 2 |
| Cyan w/graphite | Pop | | | 10/10 | | | |
| Plastic | Pop | | | 10/10 | | | |
| Marine Sealant | Pop | | | 10/10 | | | |
| AA vs. STD | p < 0.001 | p = 0.003 | p = 0.059 | p = 0.160 | p < 0.001 | p < 0.001 | p < 0.001 |
| Sc vs. STD | | | | | | | |
| Vinyl vs. STD | p < 0.001 | p = 0.010 | p = 0.653 | p = 1 | p = 0.002 | p < 0.001 | p < 0.001 |
| Cy vs. STD | p < 0.001 | p < 0.001 | p = 0.001 | p = 0.027 | p < 0.001 | p < 0.001 | p = 0.009 |
| Cy/g vs. STD | | | | | | | |
| Pl vs. STD p-value | | | | | | | |
| MS vs. STD p-value | | | | | | | |

Example 10—Effect of Partial Insulation on Targeted Myocardial Tissue Temperature Dispersion During a 30 second ablation at 50 Watts (power control mode), the mean temperatures recorded at 3 and 5 mm depths beneath the irrigated ablation catheter tip were significantly higher with ablation using an AOBN partial insulation, compared to a standard 4 mm catheter (FIG. 25). Further modification of the AOBN partial insulation with vents (FIG. 23) improved catheter tip-tissue interface temperatures, thereby overcoming any potential temperature limitations and allowing for equivalent lesion sizes. Vented AOBN achieved maximum 50 W powers (Tables 8 and 9).

TABLE 8

Myocardial Ablation Lesion Characteristics After Radiofrequency Energy Applied at 30 W (n = 20) for 60 Seconds using Arctic Alumina insulation and vented Arctic Alumina insulation

| Thermocool Catheter | Average Max Depth (mm) | Diameter Max (mm) | Max Surface Diam (mm) | Steam Pops | Volume (mm$^3$) | Impedance Drop (Ohms) | Peak temp (□) |
|---|---|---|---|---|---|---|---|
| Standard (STD) | 3.1 ± 0.3 | 7.2 ± 0.6 | 5.8 ± 0.4 | 0 | 61.3 ± 10.5 | 6 ± 1 | 37 ± 1 |
| Arctic Alumina (AA) | 4.7 ± 0.6 | 8.3 ± 1.2 | 7.0 ± 0.8 | 0 | 121.8 ± 43.3 | 26 ± 6 | 42 ± 2 |
| Vented Arctic Alumina | 3.5 ± 0.2 | 7.4 ± 0.7 | 6.2 ± 0.5 | 0 | 74.2 ± 16.6 | 8 ± 2 | 40 ± 1 |
| AA vs. STD | p < 0.001 | p = 0.001 | p < 0.001 | p = 1 | p < 0.001 | p < 0.001 | p < 0.001 |
| Vented AA vs. STD | p < 0.001 | p = 0.561 | p = 0.003 | p = 1 | p = 0.006 | p < 0.001 | p < 0.001 |
| Vented AA vs. AA | p < 0.001 | p = 0.005 | p = 0.002 | p = 1 | p < 0.001 | p < 0.001 | p = 0.001 |

TABLE 9

Myocardial Ablation Lesion Characteristics After Radiofrequency Energy Applied at 50 W (n = 20) for 60 Seconds using Arctic Alumina insulation and vented Arctic Alumina insulation

| Thermocool Catheter | Average Max Depth (mm) | Diameter Max (mm) | Max Surface Diam (mm) | Steam Pops | Volume (mm$^3$) | Impedance Drop (Ohms) | Peak temp (□) |
|---|---|---|---|---|---|---|---|
| Standard (STD) | 4.4 ± 0.3 | 8.5 ± 0.5 | 6.8 ± 0.5 | 0/20 | 115.9 ± 17.2 | 11 ± 4 | 40 ± 1 |
| Arctic Alumina (AA) | 6.2 ± 0.3 | 9.9 ± 0.7 | 7.8 ± 0.7 | 5/29 | 221.2 ± 32.7 | 33 ± 6 | 43 ± 1 |
| Vented Arctic Alumina | 5.2 ± 0.2 | 9.5 ± 0.5 | 7.4 ± 0.5 | 1/29 | 167.0 ± 16.5 | 17 ± 3 | 42 ± 2 |
| AA vs. STD | p < 0.001 | p < 0.001 | p < 0.001 | p = 0.033 | p < 0.001 | p < 0.001 | p < 0.001 |
| Vented AA vs. STD | p < 0.001 | p < 0.001 | p < 0.001 | p = 0.358 | p < 0.001 | p < 0.001 | p < 0.001 |
| Vented AA vs. AA | p < 0.001 | p = 0.032 | p = 0.028 | p = 0.085 | p < 0.001 | p < 0.001 | p = 0.002 |

Figure 26:
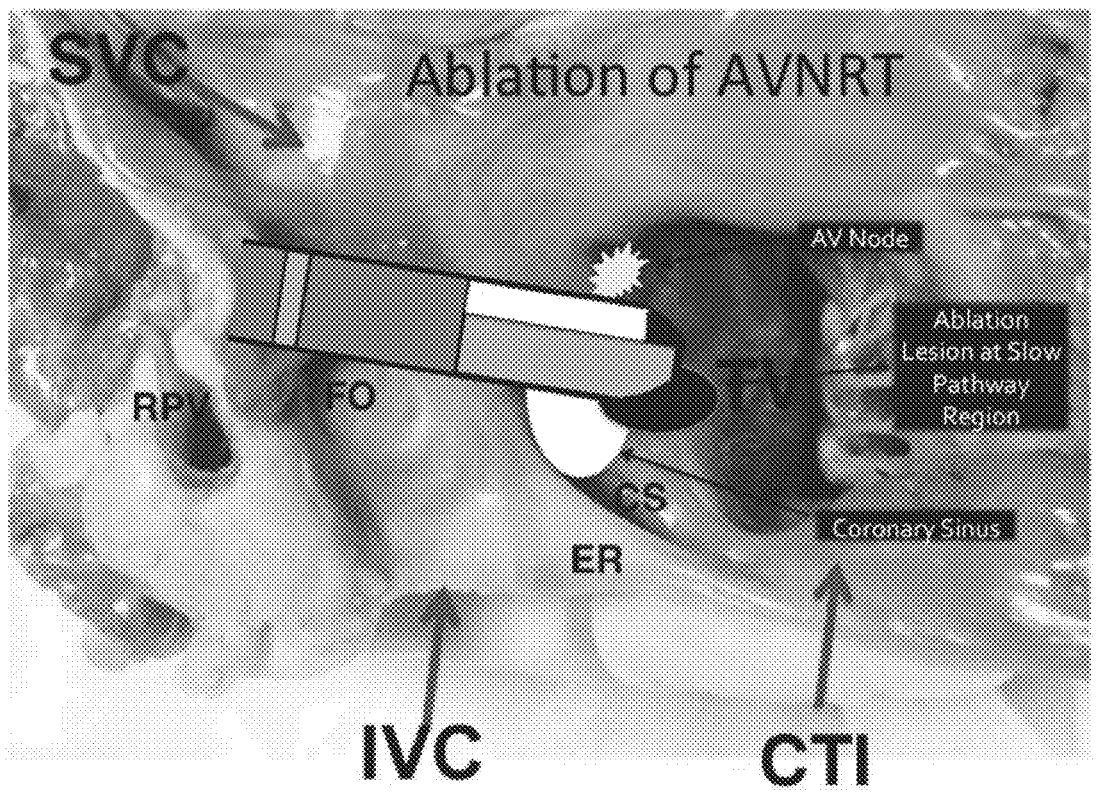
FIG. 26 is an image depicting ablation of AVNRT. During ablation of AVNRT, targeting of the slow pathway is in the triangle between the tricuspid valve and the coronary sinus, but the superior side of a standard ablation catheter applies unnecessary and unsafe RF towards the AV node. The insulated superior aspect of the PIFA mitigates this collateral damage to the AV node.

Example 11—Protection of Bundle of His and AV Node During RF Ablation with an Externally Irrigated PIFA Catheter in an In Vivo Porcine Model An example of where the PIFA catheter can potentially improve safety is in the ablation of AVNRT, where ablation of the slow pathway is in the triangle between the tricuspid valve and the coronary sinus (FIG. 26), but the superior side of a standard ablation catheter applies unnecessary and unsafe RF towards the AV node. The insulated superior aspect of the PIFA mitigates this collateral damage to the AV node.

Figure 27:
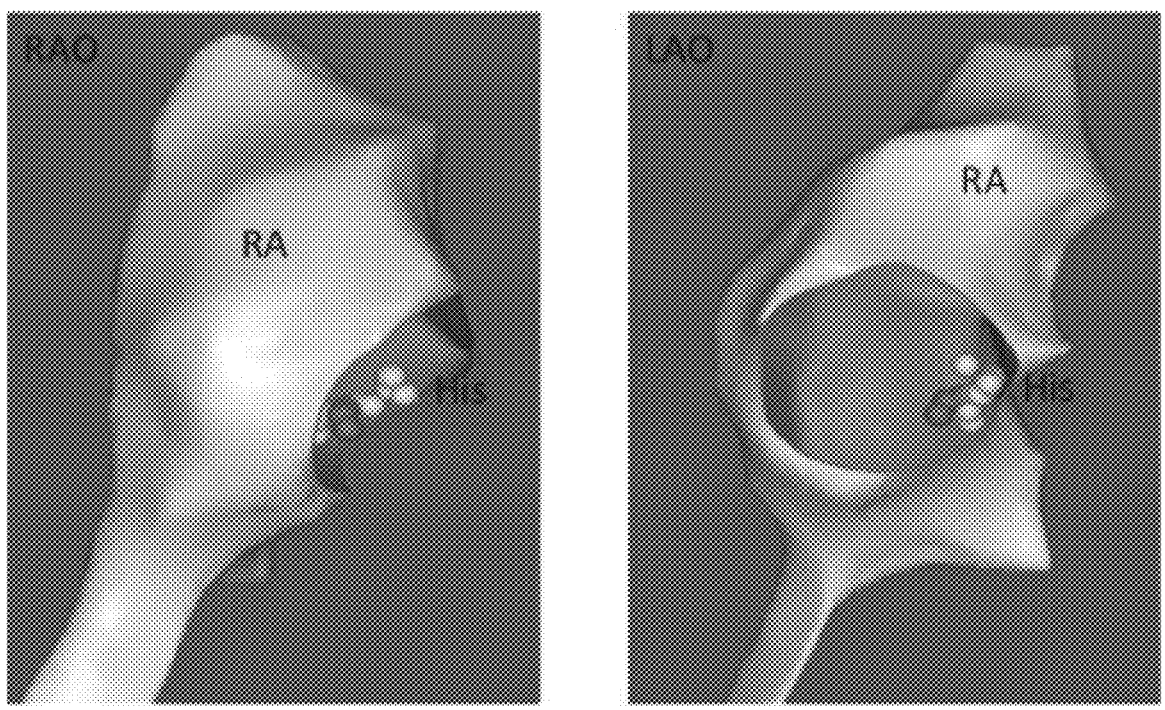
FIG. 27 is a pair of images depicting in vivo porcine ablations. During in vivo porcine ablations, ablation was performed very close to the His cloud, as demonstrated by the dark ablation lesion tags next to the light His tags. His—Bundle of His. RA—right atrium. LAO—Left anterior oblique. RAO—Right anterior oblique.
Figure 28A:
FIG. 28A is a graph illustrating ablation near the His region. Ablation near the His region with an open irrigated PIFA catheter did not result in heart block, compared to heart block occurring in all controls.
Figure 28B:
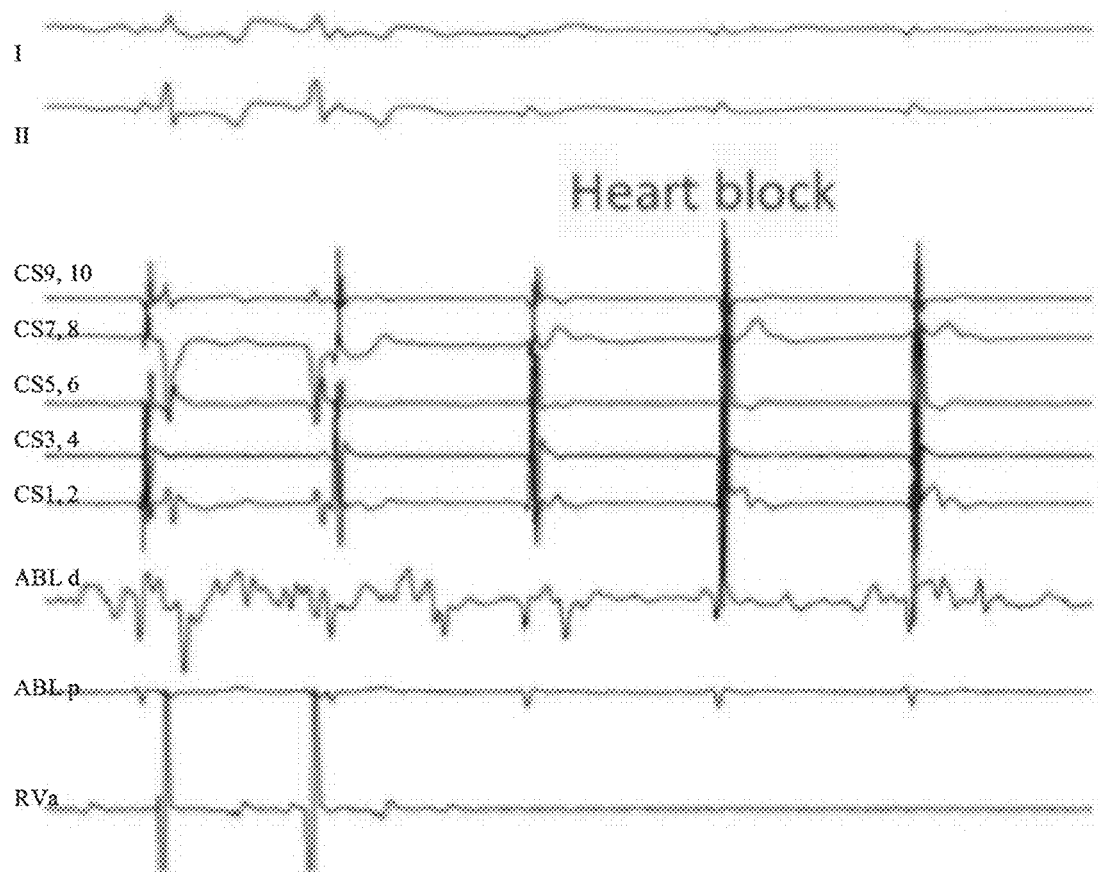
FIG. 28B is a graph illustrating ablation near the His region. Ablation near the His region with an open irrigated PIFA catheter did not result in heart block, compared to heart block occurring in all controls.
Figure 28C:
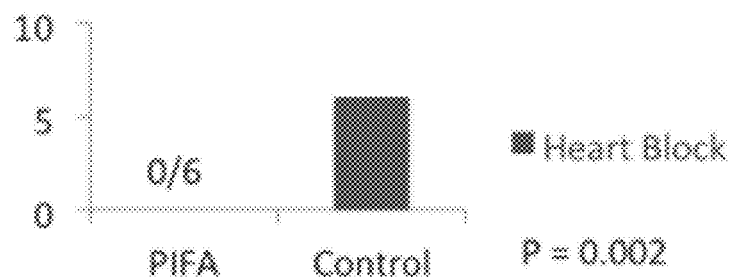
FIG. 28C is a bar graph comparing the heart block between the open irrigated PIFA catheter and the open irrigated control.

We have studied this particular application in porcine studies, where we ablated very close to the His cloud, as demonstrated by the dark ablation lesion tags next to the light His tags (FIG. 27). Ablation near the His region with an open irrigated PIFA catheter did not result in heart block (FIG. 28), n=0/6, compared to heart block occurring in all controls ablated with a non-modified irrigated catheter, n=6/6 (p=0.002).

Figure 29:
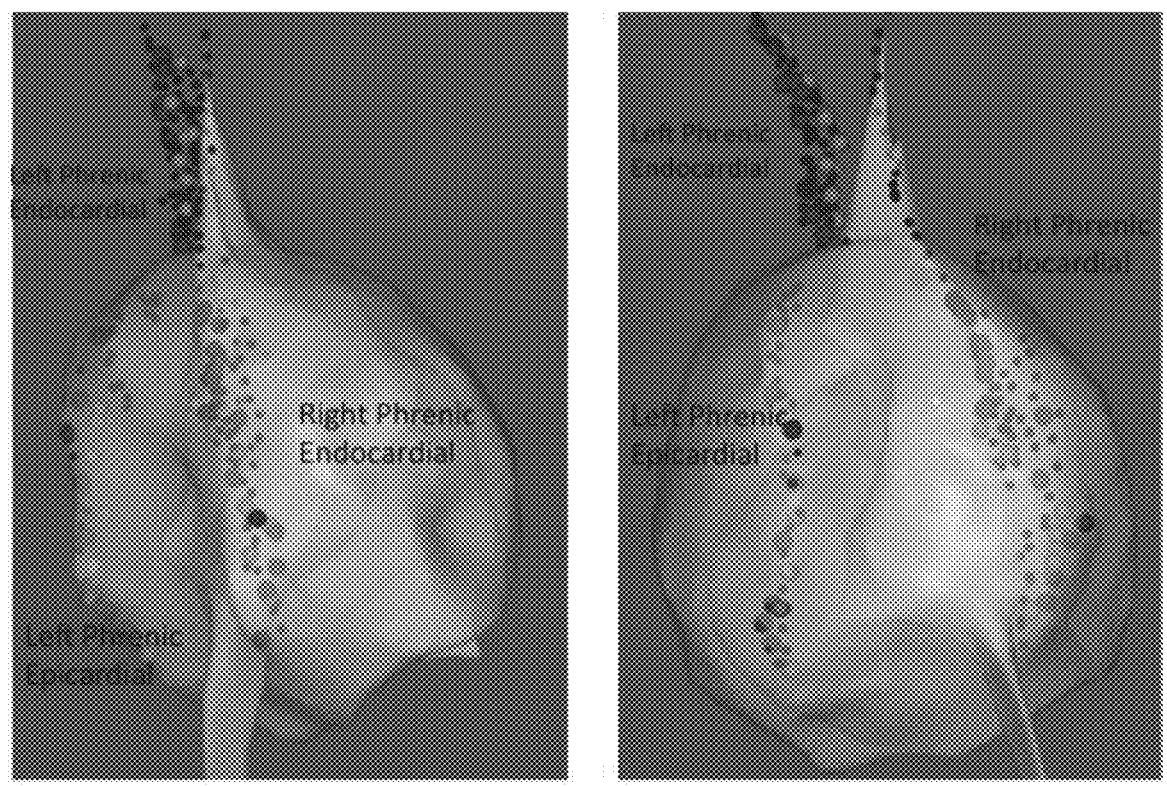
FIG. 29 is a pair of images depicting PIFA ablations. PIFA ablations, as denoted by light tags, are alternated with control ablations, denoted by dark lesion tags, for both endocardial and epicardial ablation near the right and left phrenic nerves.
Figure 30:
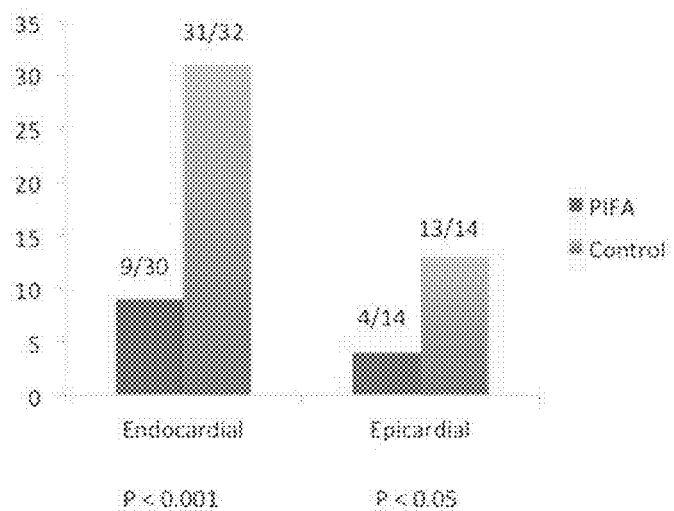
FIG. 30 is a pair of graphs illustrating that in both epicardial and endocardial ablations, PIFA caused fewer loss of phrenic nerve capture compared to controls.

Example 12—Protection of Phrenic Nerve During RF Ablation with an Externally Irrigated PIFA Catheter in an In Vivo Porcine Model Another application for PIFA is ablation near the phrenic nerve, both during atrial fibrillation and VT ablations. In these experiments, we alternate PIFA ablations, as denoted by light tags, with control ablations, denoted by dark lesion tags, for both endocardial and epicardial ablation near the right and left phrenic nerves (FIG. 29). We found that, in both epicardial and endocardial ablations, PIFA caused statistically significant fewer loss of phrenic nerve capture compared to controls (FIG. 30).

Radiofrequency ablation with partially insulated ablation catheters results in significantly altered tissue heating and lesion properties. Specifically, in the experiments presented herein, ablation of myocardial tissue with partially insulated catheters resulted in an increase in ablation lesion size and geometry beneath the non-insulated catheter tip surfaces, while myocardial tissue on the insulated sides were protected and had only minimal evidence of exposure to RF energy. The larger and asymmetric lesions created by the PIFA catheters were associated with a larger reduction in electrical impedance, which was likely due to an increase in the RF current density. Furthermore, the very thin coating of electrical insulation using a thermally conductive material resulted in insignificant tip temperatures given the same amount of power despite the lower amount of electrically active surface area compared to standard catheters using clinically relevant power settings.

By insulating a portion of a standard ablation catheter, the effective current density on the remaining non-insulated metallic tip used for RF energy delivery is greatly increased, therefore leading to larger and, depending on catheter orientation, asymmetric lesions. Furthermore, in addition to having a smaller RF conductive surface area, there may also be an enhanced "edge effect" with partial insulation, due to the resultant semi-circular exposed metal of the modified ablation catheter. Besides the increased RF current density compared to standard non-insulated catheters, the non-irrigated PIFA catheters also demonstrated significant comparative reduction in RF heating of tissue along the insulated side. However, this reduction in heating on the insulated side was not significant for the open irrigated PIFA catheter. This is likely due to the fact that the measured temperatures were at the surface of the myocardium, which would be affected by the unchanged cool saline irrigation fluid negating any effect of RF shielding at that shallow surface level. Hence, although the insulation decreased temperatures, its effects were similar to but not better than open irrigation that is actively cooling that side of the catheter at the very shallow tissue level. Analysis of the lesions created with this catheter, however, reveal tissue necrosis only inferior to the top border of the catheter, unlike non-insulated standard catheters. Because of this, structures immediately adjacent to this aspect of the catheter would be expected to be protected, as was observed in the in vivo porcine model using this catheter.

Catheter ablation of cardiac tissue with radiofrequency (RF) energy is routinely performed for the treatment of a variety of arrhythmias. All radiofrequency ablation catheters are radially symmetric at the catheter tip cylinder, thus allowing for circumferential RF. However, there is an unmet need in catheter design that allows for a more tailored approach during RF ablation in which circumferential ablation is not desired. There are many circumstances where RF energy restricted to a single side of the catheter may prevent complications due to unintended collateral injury to vital structures adjacent to the targeted cardiac tissue. This situation is most commonly observed during RF application near the AV node, in the epicardium, and near the phrenic nerve. Furthermore, a circumferential catheter tip may lead to unintended loss of RF to surrounding blood flow, thus decreasing the efficacy of ablation. An insulated catheter, where RF energy is concentrated to a single side, will allow for a more effective ablation at lower powers, potentially improving safety. It will also permit RF delivery deeper into tissues and is therefore useful for difficult arrhythmias arising from deep structures such as the septum, papillary muscle, and cavo-tricuspid isthmus.

An insulated catheter has been designed and engineered using a thin coating of thermally conductive material on half the surface of a catheter tip to direct RF energy preferentially and asymmetrically to the non-insulated side of the catheter tip. Ablation studies with these PIFA catheters have confirmed our two main hypotheses for its clinical applicability. First, we have shown that the insulated sides of the PIFA catheters have decreased temperature changes and minimal tissue injury when RF ablation is delivered. Secondly, we have shown that the non-insulated sides of these catheters deliver a greater degree of tissue heating with less power resulting in larger ablation lesions without the limitation of higher tip temperatures.

Glossary of Claim Terms

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An ablation catheter system for ablating tissue comprising:
   a catheter body including a distal tip;
   a circumferential ablation electrode at the distal tip of the catheter body; and
   an insulating layer disposed over the circumferential ablation electrode and covering an arcuate section of a portion the circumferential electrode opposing an axis of energy emission from the circumferential electrode, the insulating layer having a plurality of openings passing there through that are configured to dissipate heat generated by the circumferential electrode away from target tissue to be ablated and reduce the dissipated heat applied to adjacent non-targeted tissue to non-ablative temperatures.

2. The ablation catheter system according to claim 1 wherein the distal tip of the ablation catheter is rotatable thereby facilitating an alteration in the orientation of the insulating layer.

3. The ablation catheter system according to claim 1 wherein the insulating layer is a thermally conductive electrical insulation.

4. The ablation catheter system according to claim 1 wherein the insulating layer is an aluminum oxide/boron nitride (AOBN) coating.

5. The ablation catheter system according to claim 1 wherein the insulating layer is selected from the group consisting of aluminum oxide, boron nitride, aluminum oxide and boron nitride composite, silicone, vinyl, polyurethane, carbon nanotubes oriented perpendicular to the RF current, graphite embedded in thermal epoxy and diamond embedded in thermal epoxy.

6. The ablation catheter system according to claim 1 wherein the circumferential ablation electrode is selected from the group consisting of a non-irrigated about 4 mm RF catheter tip, non-irrigated 8 mm RF catheter tip, and an open-irrigated RF ablation catheter tip.

7. The ablation catheter system according to claim 1 wherein the insulating layer covers about one-half of the catheter tip circumferential ablation electrode.

8. The ablation catheter system according to claim 1 further comprising one or more ports in the circumferential ablation electrode to allow for irrigation through the insulating layer.

9. The ablation catheter system according to claim 1 wherein the circumferential ablation electrode is elongate and has an inferior aspect and a superior aspect relative to the axis of elongation and the inferior aspect is adapted to contact tissue during ablation.

10. An ablation catheter system for ablating the tissue of a body comprising:
a catheter body including a distal tip;
a circumferential ablation electrode at the distal tip of the catheter body; and
an insulating layer disposed over an arcuate portion of the ablation electrode opposing the tissue to be ablated, wherein the insulating layer has a plurality of holes passing through the insulating layer and exposing portions of the ablation electrode through the plurality of holes in the insulating layer, and wherein the plurality of holes are configured to dissipate heat generated by the ablation electrode.

11. The ablation catheter system according to claim 10 wherein the insulating layer is a thermally conductive electrical insulation.

12. The ablation catheter system according to claim 10 wherein the insulating layer is an aluminum oxide/boron nitride (AOBN) coating.

13. The ablation catheter system according to claim 10 wherein the insulating layer is selected from the group consisting of aluminum oxide, boron nitride, aluminum oxide and boron nitride composite, silicone, vinyl, polyurethane, carbon nanotubes oriented perpendicular to the RF current, graphite embedded in thermal epoxy and diamond embedded in thermal epoxy.

14. An interchangeable ablation catheter tip for a radiofrequency ablation catheter comprising:
a circumferential ablation electrode, the ablation electrode comprising an insulating layer disposed over a portion of the ablation electrode that is opposite an axis of energy emission from the ablation electrode;
a plurality of vent openings passing through the insulating later and configured to dissipate heat generated by the ablation electrode away from targeted tissue and reduce the heat to sub-ablative temperatures; and
a connector, wherein the connector physically and electrically connects the interchangeable ablation catheter tip to a radiofrequency ablation catheter and the connector is adapted to releasably engage the interchangeable ablation catheter tip to the radiofrequency ablation catheter.

15. The interchangeable ablation catheter tip according to claim 14 wherein the circumferential ablation electrode is selected from the group consisting of a non-irrigated about 4 mm RF circumferential ablation electrode, non-irrigated 8 mm RF circumferential ablation electrode, and an open-irrigated RF circumferential ablation electrode.

16. The interchangeable circumferential ablation electrode according to claim 14 wherein the insulating layer covers about one-half of the circumferential ablation electrode.

17. The interchangeable circumferential ablation electrode according to claim 14 further comprising one or more ports in the insulating layer to allow for irrigation through the insulating layer.

18. The interchangeable circumferential ablation electrode according to claim 14 wherein the insulating layer has a plurality of holes dispersed over the insulating layer thereby exposing portions of the ablation electrode through the holes in the insulating layer.

19. The interchangeable circumferential ablation electrode according to claim 14 wherein the insulating layer is selected from the group consisting of aluminum oxide, boron nitride, aluminum oxide and boron nitride composite, silicone, vinyl, polyurethane, carbon nanotubes oriented perpendicular to the RF current, graphite embedded in thermal epoxy and diamond embedded in thermal epoxy.

20. The interchangeable ablation catheter tip according to claim 14 wherein the connector has threads that engage complementary threads on the radiofrequency ablation catheter.

21. An ablation catheter system comprising:
an elongated catheter body including a distal tip;
a plurality of interchangeable ablation catheter tips for a radiofrequency ablation catheter according to claim 14, wherein at least two of the plurality of tips have a different electrode size, style, or pattern of insulating layer and wherein the connector of the interchangeable ablation catheter tip connects the interchangeable ablation catheter tip to the distal tip of the catheter body.

22. An ablation catheter system comprising:
an elongated catheter body including a distal tip;
a circumferential elongated ablation electrode having a length with a first end and a second end, wherein the first end is affixed to the distal tip of the catheter body and the second end extends away from the catheter body; and
an insulating layer disposed only over a portion of the circumferential elongated ablation electrode opposite from the tissue to be ablated, wherein the insulating layer further includes a plurality of openings passing through the insulating layer which are configured to dissipate heat to non-ablated tissues.

\* \* \* \* \*